US008680485B2

(12) United States Patent
Tanabe

(10) Patent No.: US 8,680,485 B2
(45) Date of Patent: Mar. 25, 2014

(54) OPTICAL ANALYSIS METHOD USING THE DETECTION OF A SINGLE LIGHT-EMITTING PARTICLE

(71) Applicant: Olympus Corporation, Tokyo (JP)

(72) Inventor: Tetsuya Tanabe, Setagaya-ku (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/840,122

(22) Filed: Mar. 15, 2013

(65) Prior Publication Data

US 2013/0207007 A1    Aug. 15, 2013

Related U.S. Application Data

(63) Continuation of application No. PCT/JP2011/071196, filed on Sep. 16, 2011.

(30) Foreign Application Priority Data

Sep. 21, 2010  (JP) ................................. 2010-210606

(51) Int. Cl.
*G01N 21/64* (2006.01)
*G01J 1/58* (2006.01)

(52) U.S. Cl.
USPC ....................................... 250/459.1; 436/172

(58) Field of Classification Search
USPC ............................ 250/458.1, 459.1; 436/172
See application file for complete search history.

(56) References Cited

FOREIGN PATENT DOCUMENTS

| JP | 4-337446 A | 11/1992 |
|---|---|---|
| JP | 2002-507762 A | 3/2002 |
| JP | 2005-098876 A | 4/2005 |
| JP | 2007-020565 A | 2/2007 |
| JP | 4023523 B2 | 12/2007 |
| JP | 2008-116440 A | 5/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2011-002415 A | 1/2011 |
| WO | 98/16814 A1 | 4/1998 |
| WO | 99/47963 A1 | 9/1999 |
| WO | 20081080417 A1 | 7/2008 |
| WO | 20091117033 A2 | 9/2009 |
| WO | 2011/108369 A1 | 9/2011 |
| WO | 2011/108371 A1 | 9/2011 |

OTHER PUBLICATIONS

International Search Report for PCT/JP2011/071196, mailing date of Nov. 29, 2011.
Masataka Kinjo, "Single molecule protein, nucleic acid, and enzyme assays and their procedures Single molecule detection by fluorescence correlation spectroscopy", Protein, Nucleic acid Enzyme vol. 44, No. 9, 1999, pp. 1431-1438. (w/English trans).

(Continued)

*Primary Examiner* — Mark R Gaworecki
(74) *Attorney, Agent, or Firm* — Westerman, Hattori, Daniels & Adrian, LLP

(57) ABSTRACT

There is provided a method of avoiding deterioration of the accuracy in the number of detected light-emitting particles due to that two or more light-emitting particles are encompassed at a time in the light detection region in the scanning molecule counting method using an optical measurement with a confocal microscope or a multiphoton microscope. In the inventive optical analysis technique, in the detection of an individual signal indicating light of a light-emitting particle by selectively detecting a signal having an intensity beyond a threshold value as a signal indicating light of a light-emitting particle in light intensity data produced through measuring light intensity during moving the position of a light detection region in a sample solution, the threshold value is set so that a signal indicating light from a light-emitting particle encompassed in a region narrower than the light detection region will be detected selectively.

10 Claims, 10 Drawing Sheets

(56) References Cited

OTHER PUBLICATIONS

Figure 4:
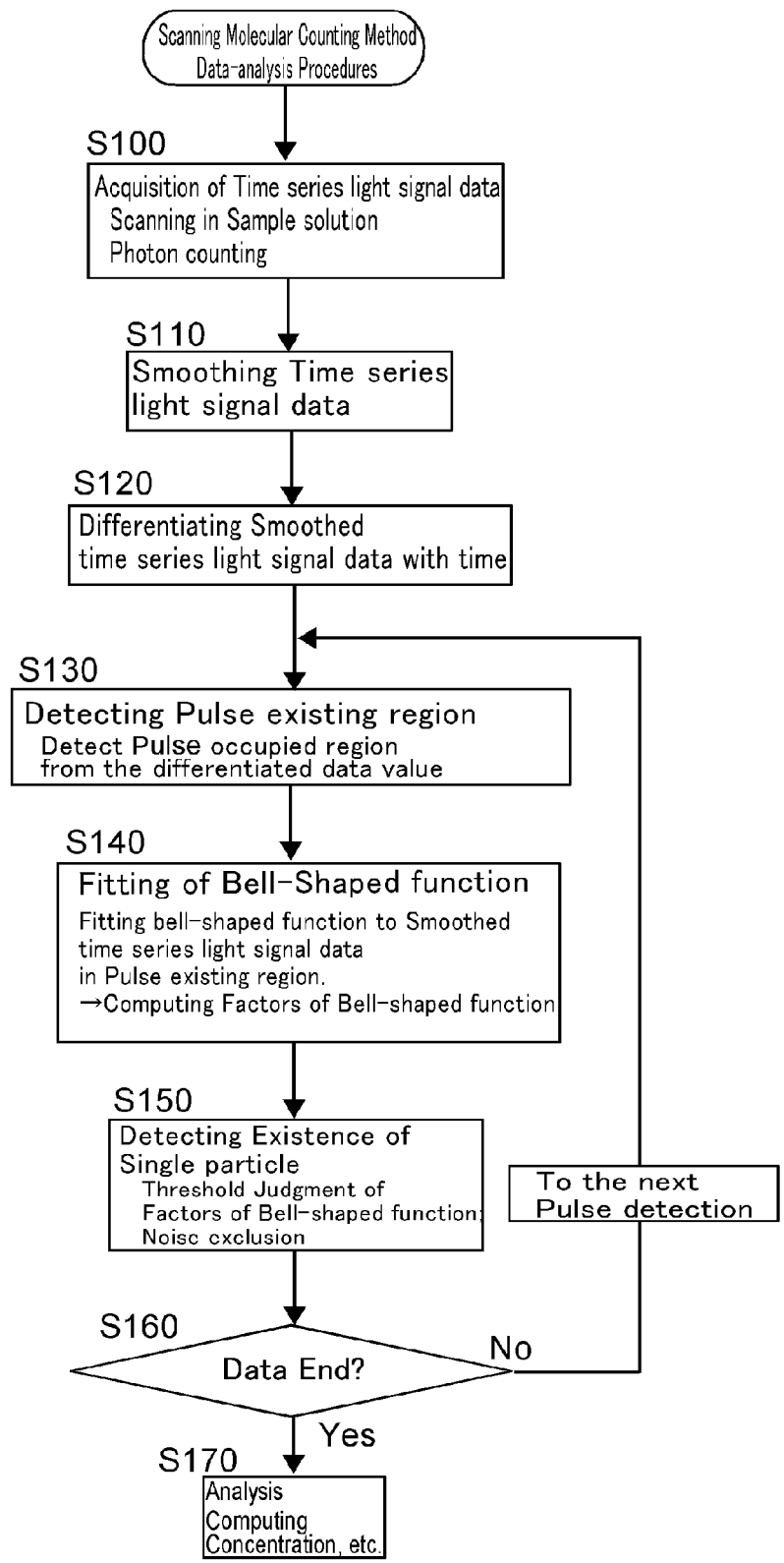

F.J. Meyer-Almes, "A new Method for Use in Molecular Diagnostics and High Throughput Pharmaceutical Screening based on Fluorescence Correlation Spectroscopy", Nanoparticle Immunoassays, R. Rigler, edit, Springer, Berlin, 2000, pp. 204-224.

Noriko Kato et al., "A single molecule analyzer that enable new analysis of DNA and protein interactions", Gene Medicine, vol. 6, No. 2, 2002, pp. 271-277.

Peet Kask et al., "Fluorescence-intensity distribution analysis and its application in biomolecular detection technology", PNAS, vol. 96, No. 24, Nov. 23, 1999, pp. 13756-13761.

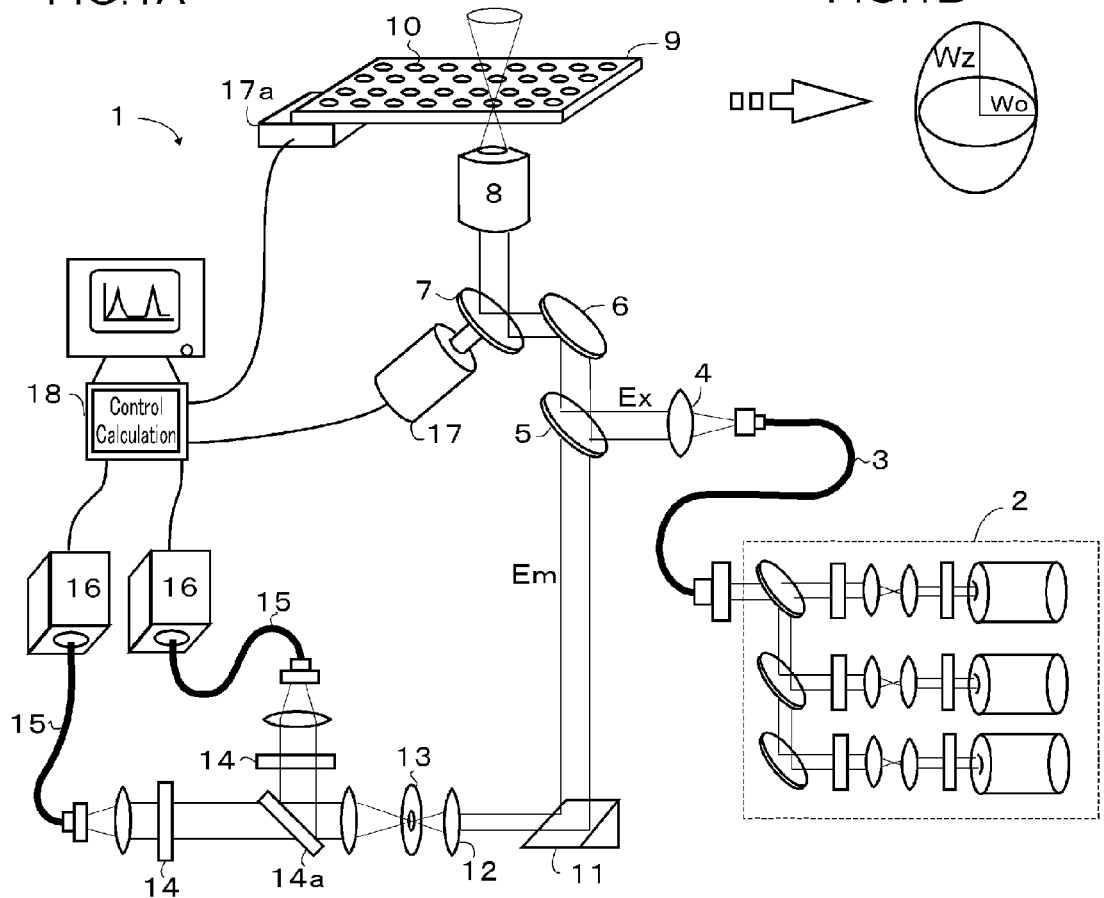
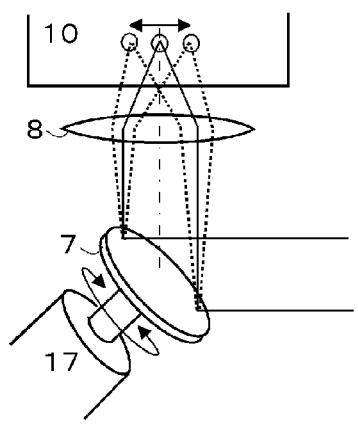
FIG.1A
FIG.1B
FIG.1C

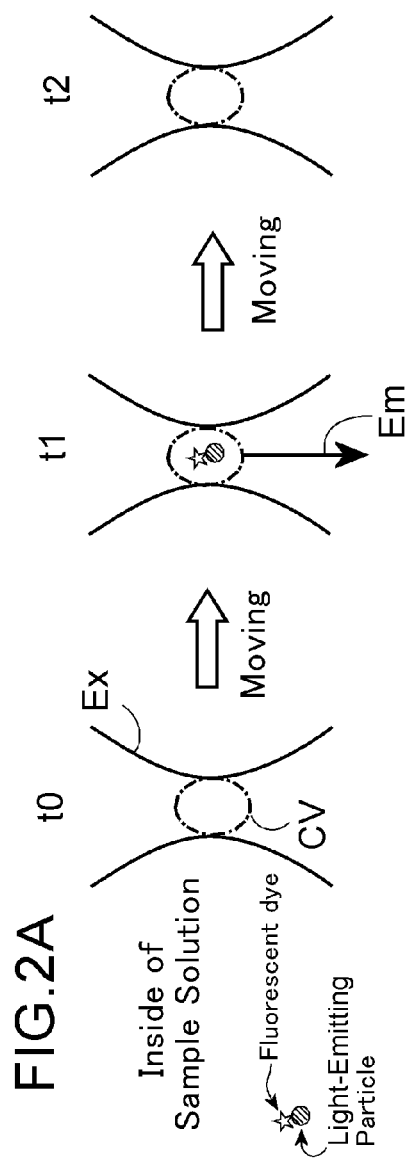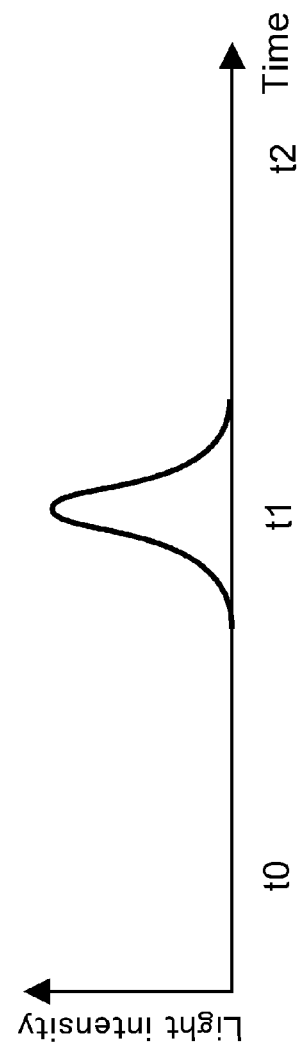

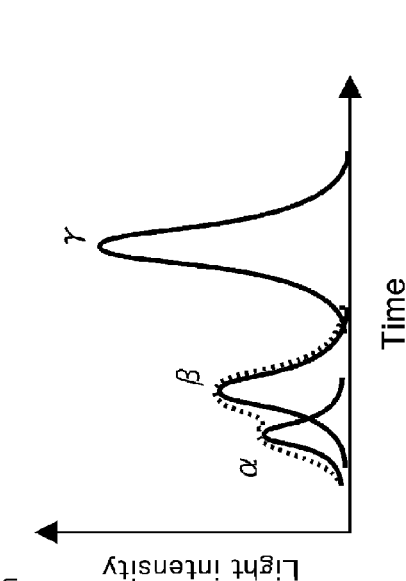
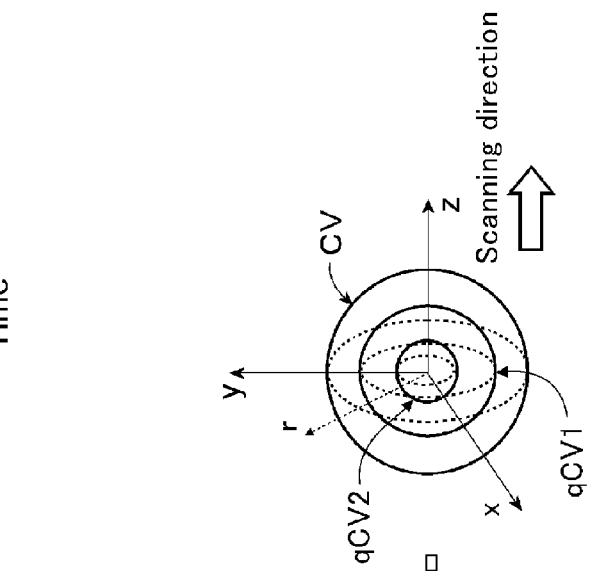
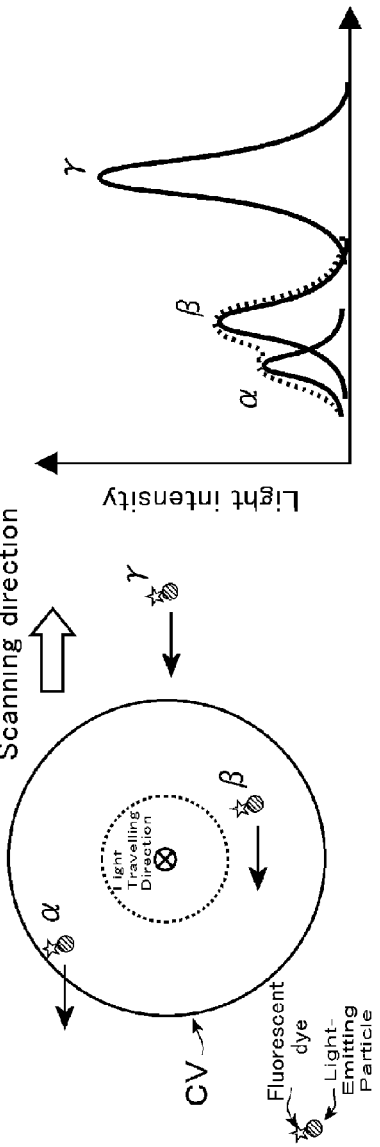
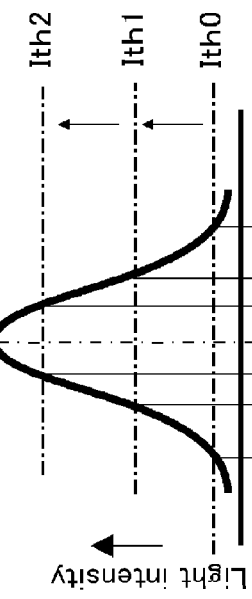
FIG.3A
FIG.3B
FIG.3C

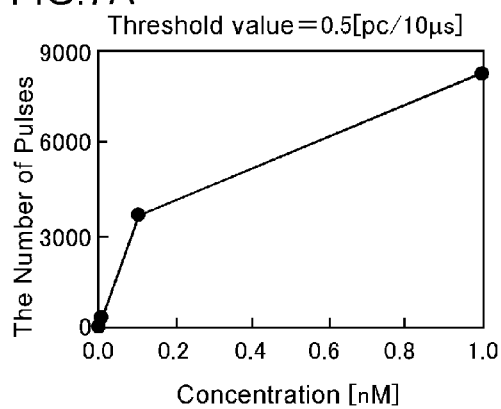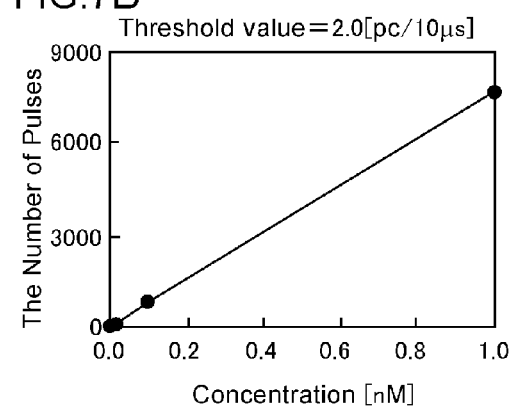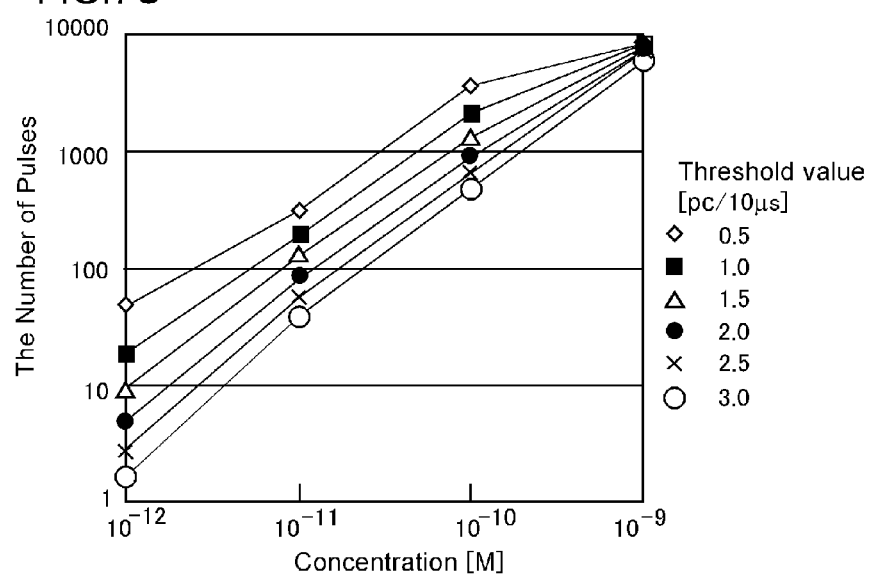

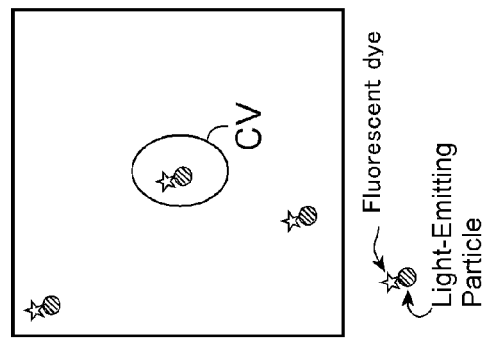
FIG.10A High Concentration (e.g. ~ 1nM)
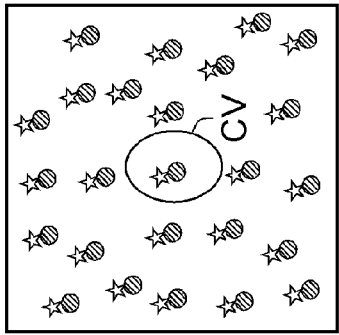
FIG.10B Low Concentration (e.g. ~ 1pM)

OPTICAL ANALYSIS METHOD USING THE DETECTION OF A SINGLE LIGHT-EMITTING PARTICLE

TECHNICAL FIELD

This invention relates to an optical analysis method capable of detecting light from a particulate object, e.g. an atom, a molecule or an aggregate thereof (Hereafter, these are called a "particle"), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to a method of detecting the light from a single particle which emits light individually, using an optical system as described above, to make it possible to conduct various optical analyses. In this regard, in this specification, a particle which emits light (hereafter, referred to as a "light-emitting particle") may be any of a particle which itself emits light and a particle to which an arbitrary light-emitting label has been attached, and the light emitted from a light-emitting particle may be fluorescence, phosphorescence, chemiluminescence, bioluminescence, scattered light, etc.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of a characteristic, an intermolecular interaction, a binding or dissociating reaction of a biological molecule, etc. by means of such a faint light measurement technique. For example, in Fluorescence Correlation Spectroscopy (FCS, see e.g. patent documents 1-3 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region (the focal region to which the laser light of the microscope is condensed, called a "confocal volume") in a sample solution, and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 4, non-patent document 4) or Photon Counting Histogram (PCH, e.g. patent document 5), there is generated a histogram of fluorescence intensity of fluorescent molecules, etc., entering into and exiting out of a confocal volume, measured similarly to FCS; and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the methods employing the measurement technique of fluorescent light of a micro region using the optical system of a confocal microscope and a photon counting technique, such as FCS and FIDA, a sample amount required for the measurement may be extremely small (an amount used in one measurement is at most several tens of μL), and its concentration is extremely low as compared with the prior art, and the measuring time is also shortened extremely (In one measurement, a measuring process for time of order of seconds is repeated several times). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446

Non-Patent Documents

Non-patent document 1: Masataka Kaneshiro; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.
Non-patent document 3: Noriko Kato, et al. "Gene medicine", Vol. 6, No. 2, pages 271-277.
Non-patent document 4: P. Kask, K. Palo, D. Ullmann, K. Gall PNAS 96, 13756-13761 (1999)

SUMMARY OF INVENTION

Technical Problem

In the above-mentioned optical analysis technique using the optical system of a confocal microscope and a photon counting technique, such as FCS, and FIDA, although the measured light is the light emitted from single or several fluorescent molecules, there are conducted in the analysis of the light the statistical procedures for the calculating of the fluorescence intensity fluctuation, etc., such as the computation of the autocorrelation function or the fitting to the histogram of fluorescence intensity data measured in time series, and therefore the signal of the light from an individual fluorescent molecule is not seen or analyzed. That is, in these optical analysis techniques, through the statistical processing of the signals of the lights from a plurality of fluorescent molecules, etc., statistical average characteristics of the fluorescent molecules, etc. will be detected. Thus, in order to obtain a statistically significant result in these optical analysis techniques, the concentration or number density of a fluorescent molecule, etc. to be an observation object in the sample solution should be at a level so that fluorescent molecules, etc. of the number enabling a statistical process will enter in and exit from a micro region in one measuring term of a length of order of seconds in an equilibrium, preferably at a level so that about one fluorescent molecule, etc. will be always present in the micro region. Actually, since the volume of a confocal volume is about 1 fL, the concentration of a fluorescent molecule, etc. in a sample solution used in the above-mentioned optical analysis technique is typically at the level of 1 nM or more, and at much less than 1 nM, there is produced a term in which no fluorescent molecules, etc. are present in the confocal volume so that no statistically significant analysis result will be obtained. On the other hand, in the detection methods of fluorescent molecules, etc. described in patent documents 6-8, no statistical computation processes of fluorescence intensity fluctuation are included so that fluorescent molecules, etc. even at less than 1 nM in a sample solution can be detected, but, it has not been achieved to compute quantitatively the concentration or number density of a fluorescent molecule, etc. moving at random in a solution.

Then, in Japanese patent application No. 2010-044714 and PCT/JP2011/53481, Applicant of the present application has proposed an optical analysis technique based on a new principle which makes it possible to observe quantitatively a condition or characteristic of a light-emitting particle in a sample solution where the concentration or number density of the light-emitting particle to be an observation object is lower than the level at which the optical analysis techniques including statistical procedures, such as FCS and FIDA, etc. are used. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. the detection region of light (called "light detection region" in the following) is moved in the sample solution, namely, the inside of the sample solution is scanned with the light detection region, and when the light detection region encompasses a light-emitting particle, dispersed and moving at random in the sample solution, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter), not only a sample amount necessary for measurement may be small (for example, about several 10 μL) and the measuring time is short similarly to optical analysis techniques, such as FCS and FIDA, but also, it becomes possible to detect the presence of a light-emitting particle and to quantitatively detect its characteristic, such as a concentration, a number density, etc., at a lower concentration or number density, as compared with the case of optical analysis techniques, such as FCS and FIDA.

By the way, in the above-mentioned scanning molecule counting method, when an increase of the light intensity corresponding to the light from a light-emitting particle, i.e., an increase of the light intensity (typically having a bell shaped profile) more than a certain threshold value, is observed in the time series data of a light intensity value (or photon count value) measured during moving the position of a light detection region within a sample solution, it is judged that one light-emitting particle has been encompassed in the light detection region, and thereby, the detection of the existence of one light-emitting particle is made. However, in this structure, because of a comparatively high concentration of the light-emitting particle in a sample solution, if two or more light-emitting particles are temporarily encompassed in the light detection region and thereby there occurs a time in which the lights of those light-emitting particles are observed simultaneously, namely, if portions of signals indicating the lights from two or more light-emitting particles overlap in time on the light intensity data, then it would become difficult to distinguish and detect separately each of the light-emitting particles, so that the information, including the number, concentration or a number density of the light-emitting particles could not be correctly acquired. Actually, as shown in an embodiment described later, it has been found out that, when a light-emitting particle concentration became high in a sample solution (about 1 nM or more), the number of detected light-emitting particles was less than the number expected from the light-emitting particle concentration in a sample solution, and the accuracy of the number of detected light-emitting particles deteriorated. This problem due to the occurrence of the condition that two or more light-emitting particles are encompassed in the light detection region at a time can be solved by changing the condensing state of the excitation light or the diameter of a pinhole to make a light detection region in the optical system of a microscope shrink so that the number of the light-emitting particles encompassed at a time in the light detection region will be substantially always one or less; but changing and adjusting the optical system for actually making the light detection region shrink are difficult, and also the structure of the device can become complicated.

However, in this respect, the inventor of the present invention has found that, by heightening a threshold value for judging an increase of the light intensity corresponding to a light-emitting particle in the light intensity data, "an apparent light detection region" can be made small and there can be obtained an operational effect almost equal to that obtained by actually making the size of a light detection region small.

In the optical analysis device for performing the scanning molecule counting method, generally, the intensity of the light which is emitted from a single light-emitting particle and reaches to a photodetector differs depending upon the position of the light-emitting particle in the light detection region, and typically, the light intensity becomes its maximum when the position of a light-emitting particle is in the approximate center region of a light detection region (Hereafter, the position at which the light intensity of the light-emitting particle in the light detection region becomes the maximum is called the "maximum intensity point"), while the light intensity gradually reduces as the position of the light-emitting particle moves closer to the circumference of the light detection region. That is, the distribution of the intensity of the detected light which is emitted from a light-emitting particle in the light detection region has an approximately bell shaped profile in which the intensity decreases from the maximum intensity point toward the circumference, and the closer to the maximum intensity point of the light detection region the passing route of the light-emitting particle during the moving of the light detection region is, the higher the light intensity of the corresponding signal becomes. Thus, the passing route of a light-emitting particle corresponding to a signal of the light intensity exceeding beyond a certain threshold value is present in a region including the maximum intensity point of the light detection region and being narrower than the light detection region, while the light intensity of a light-emitting particle which passes through the outside of the region narrower than the light detection region will be less than the above-mentioned threshold value. In addition, as the threshold value for discrimination of a signal indicating the light corresponding to a light-emitting particle on the light intensity data is made higher, the passing position of a light-emitting particle corresponding to a signal to be chosen will be limited within a narrower region. In the other words, by the increase or change of the threshold value for discrimination of a signal of a light-emitting particle, the shrinkage or regulation of "an apparent light detection region" (namely, a region in which a light-emitting particle is detected or a region through which a light-emitting particle producing a signal detected as a signal of a light-emitting particle passes) becomes possible (see the following (notes)). According to this knowledge found out by the inventor, only with a modification in the analysis processing of measured data, it becomes possible to define a region in which the number of light-emitting particles encompassed at a time is substantially always one or less even at a high light-emitting particle concentration in a sample solution, and thereby a single light-emitting particle passing through the inside of the region can be detected, so that information, such as the number, concentration, number density, etc. of light-emitting particles become accurately acquirable.

[(notes) Since it is thought that light-emitting particles are uniformly distributed in three dimensions in a sample solution, the overlapping of the peak points (the maximum points of signal intensities) of the signals of two or more light-emitting particles encompassed in the light detection region during its moving hardly occurs, and in most cases, the peak points of the signals are shifted mutually, so that the maximum values of the overlapping signals does not become as large as the peak intensity of a signal of one light-emitting particle. Further, although the more light-emitting particles passing through the outside of the apparent light detection region are present in the farer region away from the apparent light detection region, the light intensity of a light-emitting particle in the outside of the apparent light detection region is lower than that of a light-emitting particle which passes through the apparent light detection region. Thus, even when the lights of two or more light-emitting particles which pass through the outside of the apparent light detection region for a certain threshold value overlap, the maximum of the intensity of the signals of the lights is less than the threshold value in most cases, and thereby it is considered that it is not detected as the signal of a light-emitting particle, while, in most cases the signal detected as a signal of a light-emitting particle is a signal of a light-emitting particle which passed through the inside of the apparent light detection region.]

Thus, one of objects of the present invention is to provide, using the above-mentioned knowledge, a new method for avoiding the deterioration of the accuracy in the number of detected light-emitting particles due to that two or more light-emitting particles are encompassed at a time in a light detection region in a scanning molecule counting method.

Further, another object of the present invention is to avoid the deterioration of the accuracy of the number of detected light-emitting particles at a high light-emitting particle concentration in a sample solution, expanding the range of the light-emitting particle concentration in which the number of detected light-emitting particle is well measurable in the scanning molecule counting method.

Solution to Problem

According to the present invention, the above-mentioned object is achieved by an optical analysis method which detects light from a light-emitting particle dispersed and moving at random in a sample solution using an optical system of a confocal microscope or a multiphoton microscope, characterized by comprising steps of: moving a position of a light detection region of the optical system in the sample solution by changing an optical path of the optical system; measuring light intensity from the light detection region with moving the position of the light detection region in the sample solution to generate light intensity data; and individually detecting a signal indicating light of a light-emitting particle on the light intensity data; wherein in the step of individually detecting a signal indicating light of a light-emitting particle, a signal which has an intensity exceeding a threshold value is detected selectively as a signal indicating light of the light-emitting particle and the threshold value is set so that a signal indicating light from a light-emitting particle encompassed in a region narrower than the light detection region in the light detection region is detected selectively. In this structure, "a light-emitting particle dispersed and moving at random in a sample solution" may be a particle, such as an atom, a molecule or an aggregate of these, which is dispersed or dissolved in a sample solution and emits light, and it may be an arbitrary particulate matter making the Brownian motion freely in a solution without being fixed on a substrate, etc. The light-emitting particle is typically a fluorescent particle, but may be a particle which emits light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. For a light-emitting particle which emits light without illumination light, for example, a molecule which emits light according to chemiluminescence or bioluminescence, no illumination light is required in the microscope). Further, in the followings in this specification, "a signal" means "a signal expressing light from a light-emitting particle" unless noted otherwise.

As understood from the above, in the basic structure of the present invention, i.e., the scanning molecule counting method, the measurement of light intensity is sequentially performed while the position of a light detection region is moved in the sample solution, namely, while the inside of the sample solution is scanned with the light detection region.

Then, when the moving light detection region encompasses a randomly moving light-emitting particle, the light from the light-emitting particle is detected by the light detecting portion, and thereby, it is expected that the existence of one particle will be detected. Thus, in the time series light intensity data indicating sequentially detected light, a signal indicating light from a light-emitting particle is individually detected, and thereby, the individual existences of light-emitting particles are detected one by one, and accordingly, diverse information on the condition of a particle in the solution will be acquired. In that case, in the present invention, based on the knowledge described above, i.e., the knowledge that the intensity of a signal of a light-emitting particle changes with the passing position of the light-emitting particle in the light detection region, the threshold value is set so that a signal indicating light from a light-emitting particle encompassed in a region narrower than the light detection region in the light detection region will be detected selectively. According to this structure, through changing the setting of a threshold value arbitrarily, the size of "an apparent light detection region" becomes adjustable, and thus it becomes possible to detect selectively an existence of a light-emitting particle passing through an arbitrary specified region in the light detection region. In this regard, as noted, typically, an intensity distribution of detected light which is emitted from a light-emitting particle in the light detection region is a distribution in which an intensity of detected light which is emitted from the light-emitting particle reduces from a maximum intensity point in the light detection region toward a circumference of the light detection region, namely, a distribution in which light intensity reduces as the position of a light-emitting particle moves from a maximum intensity point closer to the circumference of the light detection region (Especially when a light-emitting particle is a particle which emits light when it is irradiated with excitation light and the light detection region is defined with the condensing region of the excitation light, an intensity distribution of detected light which is emitted from a light-emitting particle in the light detection region conforms with the intensity distribution of the excitation light in the light detection region). Therefore, it becomes possible to narrow down "an apparent light detection region" to a narrower region (including the maximum intensity point), as a threshold value is increased.

Further, typically, it is preferable to acquire information, including the number, concentration, etc. of light-emitting particles, by detecting a signal of a single light-emitting particle individually in the scanning molecule counting method, and therefore, in the structure of the above-mentioned present invention, preferably, the threshold value is set so that the number of the light-emitting particles encompassed at a time in a region (apparent light detection region) narrower than the light detection region will be substantially one or less. In this connection, the threshold value may be determined theoretically, for example, based on the size of the light detection region estimated from design data, so that the number of the light-emitting particles encompassed at a time in the apparent light detection region will be one or less; however, usually, it is difficult to determine the theoretical value of the size of a light detection region precisely, and therefore, a threshold value which gives an apparent light detection region which renders the number of the light-emitting particles encompassed at a time to be one or less may be determined through repeating a trial experiment several times. In this regard, as understood from the embodiment shown later, it is possible to acquire information, including the number, concentration, etc. of light-emitting particles, even if the threshold value is not set so that the number of light-emitting particles encompassed at a time in the apparent light detection region will be one or less. It should be understood that what is important in the present invention is that the size of an apparent light detection region can be set appropriately.

In one of the aspects of the above-mentioned present invention, the number of light-emitting particles encompassed in a region narrower than the light detection region (apparent light detection region) may be counted by counting the number of the selectively detected signals (The counting of particles). In that case, by associating the number of the detected light-emitting particles with the moving amount of the position of the light detection region, the information on the number density or concentration of the light-emitting particle detected in the sample solution will be acquired. Concretely, for instance, the ratio of number densities or concentrations of two or more sample solutions or a relative ratio of a number density or concentration to a standard sample solution to be the reference of a concentration or a number density may be computed, or an absolute number density value or concentration value may be determined using a relative ratio of a number density or concentration to a standard sample solution to be the reference of a concentration or a number density. Or, by determining by an arbitrary method the whole volume of the moving track of the position of the light detection region and/or, the whole volume of the apparent light detection region, for example, by moving the position of the light detection region at a predetermined speed, the number density or concentration of the light-emitting particle can be concretely computed.

Moreover, as another manner of the present invention, based on the intensity distribution of detected light which is emitted from a light-emitting particle in a light detection region, it is also possible to compute, from the number of the light-emitting particles determined by the counting of particles, the number of the light-emitting particles to be detected when a threshold value, different from the threshold value in the performing of counting of particles, is set. As described later in the column of explanation of embodiments, an intensity distribution of detected light which is emitted from a light-emitting particle in a light detection region can be approximately determined based on the number of light-emitting particles determined by the counting of particles. And, when the intensity distribution of detected light which is emitted from a light-emitting particle in a light detection region is determined, it becomes possible to estimate the size of the apparent light detection region corresponding to an arbitrary threshold value. It is considered that the number of light-emitting particles which pass through the apparent light detection region is proportional to the size of the apparent light detection region, and therefore, based on a ratio of the size of the apparent light detection region corresponding to the threshold value in performing the counting of particles and the size of the apparent light detection region for another threshold value, the number of light-emitting particles to be detected when the other threshold value is set can be computed. When the number of light-emitting particles to be detected when another threshold value different from the threshold value in performing the counting of particles is set is obtained, a comparison between the numbers of particles detected using mutually different threshold values become easy, which is advantageous in acquiring the information about a number density or concentration of a light-emitting particle, etc. In this regard, using the number of light-emitting particles to be detected when a threshold value different from the threshold value in performing the counting of particles is set, the number density or concentration of light-emitting particle may be determined.

Furthermore, a further manner of the present invention may be designed such that, in a case that a threshold value is set so that the number of light-emitting particles encompassed at a time in a region narrower than the light detection region may be substantially set to one or less, there is detected a threshold value, with which the number of selectively detected signals indicating light from a light-emitting particle becomes a predetermined number, and then, based on the magnitude of the detected threshold value, the number density or concentration of the light-emitting particle is determined. As described later in the column of embodiments, the number density or concentration of a light-emitting particle is given from the number of signals detected selectively and the size of an apparent light detection region, and both the number of signals and the size of the apparent light detection region are the functions of a threshold value (the number of signals and the size of the apparent light detection region are reduced as the threshold value becomes higher), and the size of the apparent light detection region can be expressed with parameters of the intensity distribution of detected light which is emitted from a light-emitting particle in the light detection region. Therefore, the number density or concentration of a light-emitting particle can be shown with a threshold value, a parameter of an intensity distribution of detected light which is emitted from a light-emitting particle in the light detection region and the number of selectively detected signal, and thus, by detecting the threshold value which gives a certain number of selectively detected signals, it becomes possible to determine the number density or concentration of a light-emitting particle. Actually, according to an experimental example described later, it has been found that the number density or concentration of a light-emitting particle is determinable from a threshold value which gives a certain number of selectively detected signals. This manner can be advantageously used in order to detect the number density or concentration of a light-emitting particle in an arbitrary sample solution in the scanning molecule counting method.

With respect to the step of moving the position of the light detection region in the above-mentioned inventive structure, the moving speed of the position of the light detection region in the sample solution is appropriately changed based on the characteristic or the number density or concentration of the light-emitting particle in the sample solution. The condition of detected light from the light-emitting particle may change in accordance with its characteristic, number density or concentration in the sample solution. Especially, when the moving speed of the light detection region becomes quick, the amount of light obtained from one light-emitting particle will be reduced, and therefore it is preferable that the moving speed of the light detection region can be changed appropriately so that the light from one light-emitting particle can be measured precisely or with sufficient sensitivity.

Furthermore, with respect to the above-mentioned step of moving the position of the light detection region, the moving speed of the position of the light detection region in the sample solution is preferably set to be higher than the diffusional moving velocity of a light-emitting particle (the average moving speed of a particle owing to the Brownian motion). As explained above, in the inventive method, the light detection region detects the light emitted from a light-emitting particle, so that the light-emitting particle will be detected individually. However, when a light-emitting particle moves at random owing to the Brownian motion to move into and out of the light detection region multiple times, it is possible that the signal from one light-emitting particle (showing its existence) will be detected multiple times, and therefore it would become difficult to make the existence of one light-emitting particle associated with the detected signal. Then, as described above, the moving speed of the light detection region is set higher than the diffusional moving velocity of the light-emitting particle, and thereby it becomes possible to make one light-emitting particle correspond to one signal. In this regard, since the diffusional moving velocity differs depending upon light-emitting particles, it is preferable that the moving speed of the light detection region can be changed appropriately according to the characteristics (especially, the diffusion constant) of the light-emitting particle as described above.

The changing of the optical path of the optical system for moving the position of the light detection region may be done in an arbitrary way. For example, the position of the light detection region may be changed by changing the optical path using a galvanomirror employed in the laser scan type optical microscope. The movement track of the position of the light detection region may be set arbitrarily, for example, which is selectable from circular, elliptical, rectangular, straight and curvilinear ones. In this connection, in the present invention, since the position of the light detection region is moved by changing the optical path of an optical system, the movement of the light detection region is quick without substantial generation of mechanical vibration and hydrodynamic effect in the sample solution, and therefore, the measurement of light can be performed under a stable condition without dynamic action affecting the light-emitting particle in the sample solution (without artifact) (For example, when a flow is generated in the sample, not only making the flow velocity always uniform is difficult, but also the device structure would become complicated, and furthermore, not only the required sample amount is substantially increased, but also it is possible that light-emitting particles or other substances in a solution would deteriorate or be denaturalized by the hydrodynamic action of the flow). Further, since no structure for flowing a sample solution is required, the measurement and analysis can be conducted with a small amount of the sample solution (at the level of one to several tens of μL) similarly to FCS and FIDA, etc.

The inventive method is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also.

Effect of Invention

Generally, in the inventive method, noticing that, in the scanning molecule counting method, since the intensity of a signal of a light-emitting particle differs depending upon the position through which the light-emitting particle passes in the light detection region, the size of an "apparent light detection region" is adjustable by changing the setting of the threshold value for judgment of a signal of a light-emitting particle, an "apparent light detection region" (a region narrower than the light detection region in the light detection region) is defined by setting a threshold value appropriately and it is tried to detect selectively a signal indicating light from a light-emitting particle encompassed in the "apparent light detection region". According to this structure of the present invention, since the region seen in detecting a signal of a light-emitting particle (apparent light detection region) becomes relatively narrower than an actual light detection region, the possibility that two or more number of light-emitting particles are encompassed in the region becomes lower than the possibility that the number of light-emitting particles in the actual light detection region is two or more, and therefore, it becomes possible to measure more correctly the number of single light-emitting particles, thereby acquiring the information about a concentration or a number density of a light-emitting particle, etc. Thus, even in a case that a light-emitting particle concentration in a sample solution becomes comparatively high so that the possibility that the number of the light-emitting particles in the actual light detection region becomes two or more could become high, a condition in which the number of light-emitting particle encompassed at a time in a region seen in detecting a signal of a light-emitting particle becomes one or less can be realized by setting the threshold value appropriately, whereby the individual detection of single light-emitting particles, the counting of their number, the acquisition of the information about a concentration or a number density of the single light-emitting particle become possible. In the other words, according to the present invention, it becomes possible to expand the concentration range or number density range of a light-emitting particle at which the scanning molecule counting method can be performed in good accuracy to the higher concentration or density side. Thus, according to the inventive method, the range of sample solutions for which the scanning molecule counting method is usable is expanded, and it is expected that the application range of the scanning molecule counting method, such as an observation and analysis of an intermolecular interaction, will be broadened.

Other purposes and advantages of the present inventions will become clear by explanations of the following preferable embodiments of the present invention.

BRIEF DESCRIPTIONS OF DRAWINGS

FIG. 1A is a schematic diagram of the internal structure of the optical analysis device with which the present invention is performed. FIG. 1B is a schematic diagram of a confocal volume (an observation region of a confocal microscope). FIG. 1C is a schematic diagram of the mechanism for changing the direction of the mirror 7 to move the position of a light detection region in a sample solution.

FIGS. 2A and 2B are a schematic diagram explaining the principle of the light detection and a schematic diagram of the variation of the measured light intensity with time in the scanning molecule counting method to which the inventive method is applied, respectively.

FIG. 3 are drawings explaining about the principle for setting an apparent light detection region by setting appropriately a threshold value for judging a signal of a light-emitting particle in accordance with the inventive method. FIG. 3A is a schematic diagram of a cross sectional view of a light detection region seen from the traveling direction of light in the microscope, schematically showing a condition that two or more light-emitting particles are encompassed at a time in the light detection region CV. FIG. 3B is a schematic diagram of an example of time series light intensity data measured in FIG. 3A. FIG. 3C is a drawing explaining about the relation among an intensity distribution of detected light which is emitted from a light-emitting particle in a light detection region, a threshold value and an apparent light detection region. The upper left is an intensity distribution of detected light which is emitted from a light-emitting particle in the light detection region; the lower right is a typical perspective diagram of the light detection region CV and apparent light detection regions qCV1 and qCV2; and the lower left is a typical sectional diagram of the light detection region CV, and the apparent light detection regions qCV1 and qCV2, seen from the moving direction of the light detection region.

FIG. 4 is a diagram showing in the form of a flow chart the procedures of the scanning molecule counting method performed in accordance with the inventive method.

Figure 5A:
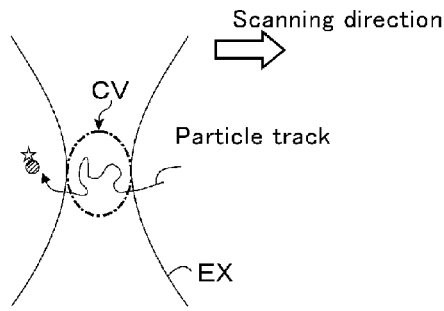

FIGS. 5A) and 5B are drawings of models in a case that a light-emitting particle crosses a light detection region owing to Brownian motion and in a case that a light-emitting particle crosses a light detection region by moving the position of the light detection region in a sample solution at a velocity quicker than the diffusional moving velocity of the light-emitting particle. FIG. 5C shows drawings explaining the example of the signal processing step of the detected signals in the procedure for detecting the existence of a light-emitting particle from the measured time series light intensity data (change in time of photon count) in accordance with the scanning molecule counting method.

Figure 6:
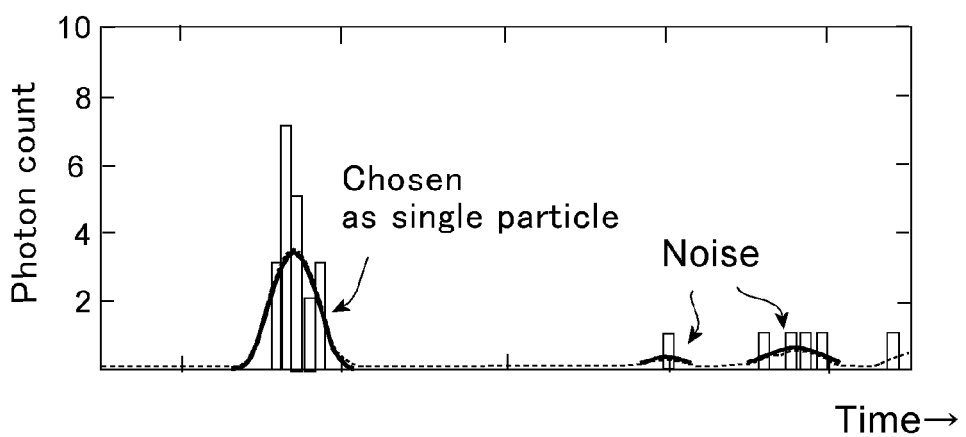

FIG. 6 shows examples of measured photon count data (bar graph); curves obtained by carrying out the smoothing of the data (dotted line); and Gauss functions fitted on the pulse existing region (solid line). In the drawing, the signals attached with "noise" are disregarded as signals due to noises or a contaminant.

FIG. 7 are graphs of the numbers of pulses detected as a signal of a light-emitting particle measured by the scanning molecule counting method (Embodiment 1) performed in accordance with the inventive method with respect to sample solutions containing various light-emitting particle concentrations. FIGS. 7A and 7B each are diagrams in which the numbers of pulses are plotted against light-emitting particle concentration in cases of the threshold value=0.5 [pc/10 μsec.] (photon number detected in 10 μsec.), and the threshold value=2.0 [pc/10 μsec.] in detecting a signal of a light-emitting particle; and FIG. 7C is a diagram in which the numbers of pulses with various threshold values are plotted against light-emitting particle concentration (the abscissa and ordinate are in logarithm).

Figure 8B:
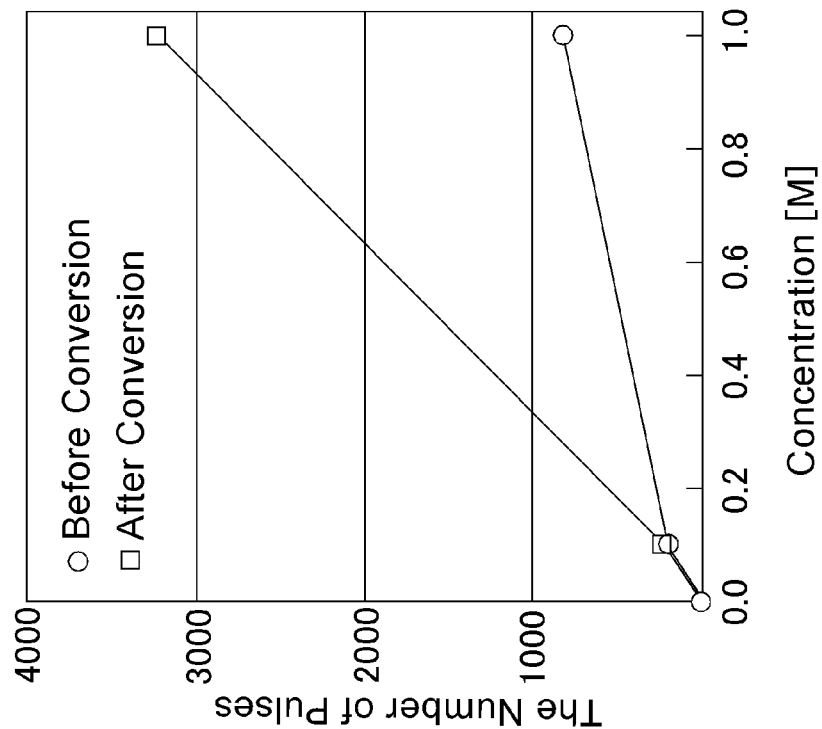
Figure 8A:
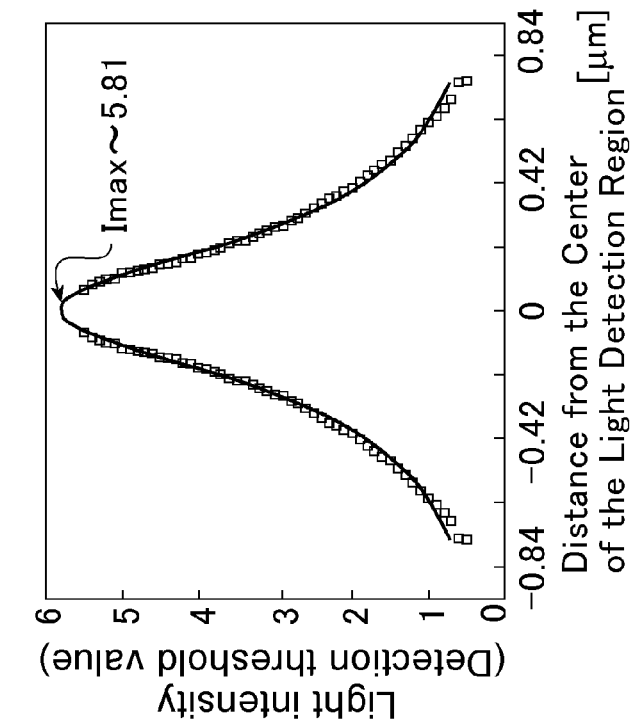

FIG. 8A shows an intensity distribution of detected light which is emitted from a light-emitting particle in a light detection region obtained from a relation between a threshold value and the number of signals of light-emitting particles; FIG. 8B is a drawing in which the numbers of pulses are plotted against light-emitting particle concentration in the case that the numbers of pulses of light-emitting particles obtained by setting a high threshold value are converted into the number of pulses to be obtained when a low threshold value is set based on the light intensity distribution of FIG. 8A.

Figure 9:
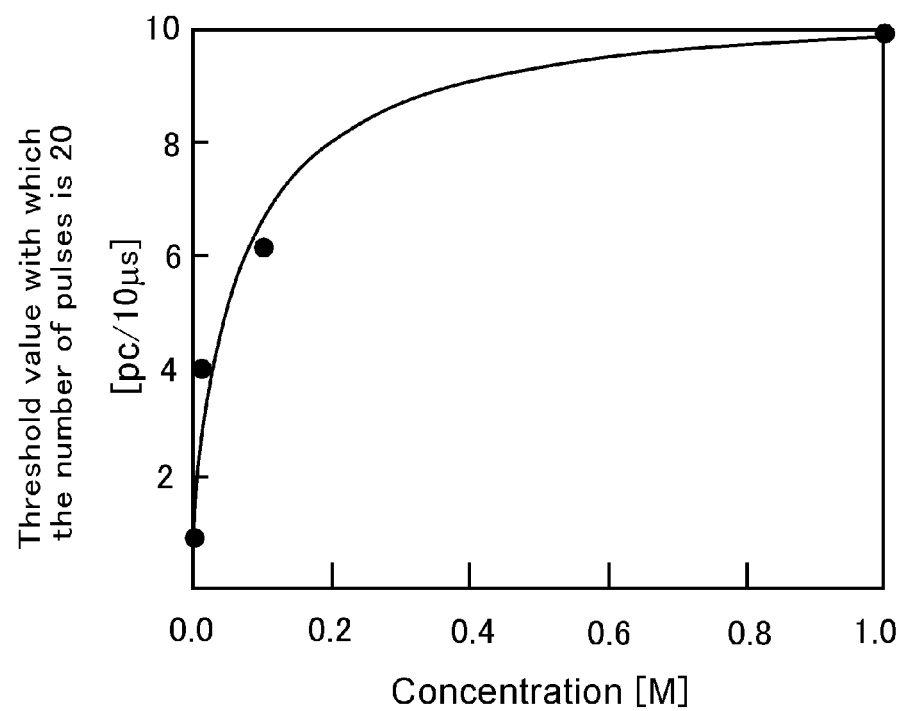

FIG. 9 is a drawing in which threshold values with which the number of pulses was 20 were plotted against light-emitting particle concentration. In the drawing, black points are threshold values and the solid line is a fitting curve to the threshold values.

FIG. 10 show examples of the time variation of the photon count (light intensity) obtained in a conventional optical analysis technique computing fluorescence intensity fluctuation, where FIG. 10A shows a case that the particle concentration is at a level providing a sufficient precision in the measurement, and FIG. 10B shows a case that the particle concentration in a sample is significantly lower than the case of FIG. 10A.

| Explanations of Reference Numerals | |
|---|---|
| 1 | Optical analysis device (confocal microscope) |
| 2 | Light source |
| 3 | Single mode optical fiber |
| 4 | Collimating lens |
| 5, 14a | Dichroic mirror |
| 6, 7, 11 | Reflective mirror |
| 8 | Objective |
| 9 | Micro plate |
| 10 | Well (sample solution container) |
| 12 | Condenser lens |
| 13 | Pinhole |
| 14 | Barrier filter |
| 15 | Multi-mode optical fiber |
| 16 | Photodetector |
| 17 | Mirror deflector |
| 17a | Stage position changing apparatus |
| 18 | Computer |

DESCRIPTION OF EMBODIMENTS

In the followings, preferable embodiments of the present invention are described in detail.

Structure of Optical Analysis Device

In the basic structure, the method according to the present invention can be realized with an optical analysis device constructed by associating the optical system of a confocal microscope and a photodetector, enabling FCS, FIDA, etc., as schematically illustrated in FIG. 1A. Referring to FIG. 1A, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light emitted from a light source 2 and transmitted through the inside of a single mode fiber 3 (Ex) forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of µL of a sample solution is dispensed, and the laser light emitted from the objective 8 is focused in the sample solution in the sample container or well 10, forming a region having strong light intensity (excitation region). In the sample solution, light-emitting particles to be observed objects, which are typically molecules to which a light emitting label such as a fluorescent dye is attached, are dispersed or dissolved, and when a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13. In this regard, as known in ones skilled in the art, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the focal plane is blocked. The focal region of the laser light illustrated in FIG. 1B is a light detection region, whose effective volume is usually about 1-10 fL, in this optical analysis device, which is called as "confocal volume". In the confocal volume, typically, the light intensity is spread in accordance with a Gaussian type or Lorentz type distribution having the peak at the center of the region, and the effective volume is a volume of an approximate ellipsoid bordering a surface where the light intensity reduced to $1/e^2$ of the peak intensity. Then, the light having passed through the pinhole 13 passes through the dichroic mirror 14a and transmits through the corresponding barrier filter 14 (where a light component only in a specific wavelength band is selected); and is introduced into a multi-mode fiber 15, reaching to the corresponding photodetector 16, and after the conversion into time series electric signals, the signals are inputted into the computer 18, where the processes for optical analyses are executed in manners explained later. For the photodetectors 16, preferably, super high sensitive photodetectors, usable for the photon counting, are used, so that the light from one light-emitting particle, for example, the faint light from one or several fluorescent dye molecule(s), can be detected.

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C. This mirror deflector 17 may be the same as that of a galvanomirror device equipped on a usual laser scan type microscope. Also, in order to attain a desired moving pattern of the position of the light detection region, the mirror deflector 17 is driven in harmony with the light detection of the photodetector 16 under the control of the computer 18. The movement track of the position of the light detection region may be arbitrarily selected from circular, elliptical, rectangular, straight and curvilinear ones, or a combination of these (The program in the computer 18 may be designed so that various moving patterns can be selected). In this regard, although not illustrated, the position of the light detection region may be moved in the vertical direction by moving the objective 8 up and down. As noted, according to the structure of changing the optical path of the optical system to move the position of the light detection region instead of moving the sample solution, neither mechanical vibration nor hydrodynamic action occur substantially in the sample solution, so that it becomes possible to eliminate the influence of a dynamic action on an object to be observed, achieving the stable measurement.

Also, for an additional structure, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18.

In the case that a light-emitting particle emits light by multiple photon absorption, the above-mentioned optical system is used as a multiphoton microscope. In that case, since the light is emitted only from the focal region of the excitation light (light detection region), the pinhole 13 may be removed. When a light-emitting particle emits light owing to phosphorescence or scattered light, the above-mentioned optical system of the confocal microscope is used as it is. Further, in the case that a light-emitting particle emits light owing to a chemiluminescence or bioluminescence phenomenon without excitation light, the optical system 2-5 for generating excitation light may be omitted. Furthermore, in the optical analysis device 1, as shown in the drawing, two or more excitation light sources 2 may be provided so that the wavelength of the excitation light can be appropriately selected in accordance with the wavelength of the light for exciting a light-emitting particle. Similarly, two or more photodetectors 16 may also be provided so as to detect the lights from light-emitting particles of two or more kinds having different light-emitting wavelengths, if contained in a sample, separately depending upon the wavelengths.

The Principle of the Inventive Method

As described in the column of "Summary of Invention", briefly, in the inventive method, based on the principle that, in the light detection with a confocal microscope (or a multiphoton microscope) as described above, the intensity of a signal of a light-emitting particle varies depending upon the position of the light-emitting particle in the light detection region so that the size of an "apparent light detection region" can be changed by the setting of a threshold value for judging a signal of a light-emitting particle, the size of an "apparent light detection region" is adjusted by setting a threshold value appropriately in the scanning molecule counting method. And, preferably, a threshold value for judging a signal of a light-emitting particle is set in order that the number of light-emitting particles encompassed at a time in an "apparent light detection region" will become one or less, that is, in order that each signal detected as a signal of a light-emitting particle will correspond to a single light-emitting particle, or in order that a single light-emitting particle will be detected surely individually, and under that condition, the number of light-emitting particles during the scanning of the inside of a sample solution with the light detection region is counted, and thereby it is tried to acquire information, including a concentration or a number density of a light-emitting particle in higher accuracy. In the following, the principles of the scanning molecule counting method and the inventive method are described.

1. Principle of Scanning Molecule Counting Method

Spectral analysis techniques, such as FCS, FIDA, etc., are advantageous in that the required sample amount is extremely small and a test can be performed promptly as compared with the conventional biochemical analytical techniques. However, in these spectral analysis techniques such as FCS, FIDA, etc., the concentration and characteristics of a light-emitting particle are principally computed based on the fluorescence intensity fluctuation, and therefore, in order to obtain accurate measurement results, the concentration or number density of the light-emitting particle in a sample solution should be at a level where about one light-emitting particle always exists in a light detection region CV during the fluorescence intensity measurement as schematically drawn in FIG. 10A so that significant light intensity (photon count) can be always detected in the measuring term as shown in the right-hand side of the drawing. When the concentration or number density of the light-emitting particle is lower than that, for example, at the level where the light-emitting particle rarely enters into the light detection region CV as drawn on FIG. 10B, no significant light intensity signal (photon count) would appear in a part of the measuring term as illustrated on the right-hand side of the drawing, and thus, accurate computation of light intensity fluctuation would become difficult. Also, when the concentration of the light-emitting particle is significantly lower than the level where about one light-emitting particle always exists in the inside of the light detection region during the measurement, the calculation of light intensity fluctuation would become subject to the influence of the background, and the measuring term should be made long in order to obtain the significant quantity of the light intensity data (photon count) sufficient for the calculation.

Then, in the Japanese patent application no. 2010-044714, and PCT/JP2011/53481, the applicant of the present application has proposed "Scanning molecule counting method" based on a new principle which enables the detection of characteristics of a light-emitting particle, such as its number density or concentration, even when the concentration of the light-emitting particle is lower than the level requested in the above-mentioned spectral analysis techniques, such as FCS and FIDA.

In the scanning molecule counting method, briefly speaking, as the processes to be performed, the light detection is performed together with moving the position of the light detection region CV in a sample solution, namely, scanning the inside of the sample solution with the light detection region CV by driving the mechanism (mirror deflector 17) for moving the position of the light detection region to change the optical path as schematically drawn in FIG. 2. Then, for example, as in FIG. 2A, during the moving of the light detection region CV (in the drawing, time to-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. In the principle of the scanning molecule counting method, no statistical calculation processes, such as the calculation of the fluorescence intensity fluctuation, are conducted and the light-emitting particles are one by one detected, and therefore, the information about the concentration or number density of the particle is acquirable even in a sample solution with a low particle concentration at the level where no sufficiently accurate analysis is available in FCS, FIDA, etc.

2. Principle of Adjustment of Size of "Apparent Light Detection Region" in Accordance with the Present Invention In the above-mentioned scanning molecule counting method, when the number density of a light-emitting particle in a sample solution is high, the possibility that two or more light-emitting particles are encompassed at a time in a light detection region becomes high. For example, as schematically drawn in FIG. 3A, if a light-emitting particle β enters into the light detection region before a light-emitting particle α exits out of the light detection region during the moving of the light detection region CV, portions of the signal of the light-emitting particle α and the signal of the light-emitting particle β will overlap mutually on the time series light intensity data, as shown in the right side of FIG. 3B. In that case, as shown with the dotted line in the drawing, the profiles of the signals of the light-emitting particles α and β become shapes which make it difficult to detect the signals of these two light-emitting particles independently, and therefore, the mutually overlapping signals of two or more light-emitting particles could be detected as a signal of one light-emitting particle. Actually, it has been found that, when the number density of a light-emitting particle in a sample solution is high, typically, when it is heightened to about 1 nM, the number of signals detected as a light of a light-emitting particle in the scanning molecule counting method reduces significantly than the number expected from the actual concentration, and this reduction of the number of signals is considered to be because the mutually overlapping signals of two or more light-emitting particles have been counted as a signal of one light-emitting particle. As one way of eliminating mutually overlapping signal of two or more light-emitting particles as described above and generating the time series light intensity data in which each single light-emitting particle can be detected individually, it is considered to make the light detection region shrink as drawn with the dotted line in FIG. 3A, attaining a condition that the number of light-emitting particle encompassed at a time in the light detection region is always substantially one or less. However, there is a theoretical limit in reduction of a light detection region (The size of the region cannot be reduced below the wavelength of light), and also, the structure of the device becomes complicated, and therefore, it is very difficult to actually make a light detection region shrink.

However, according to the present invention, only through a correction in the signal processing in detecting a signal of a light-emitting particle from time series light intensity data, the signal of light of a light-emitting particle which passes through a region narrower than the light detection region in the light detection region as drawn with the dotted line in FIG. 3A becomes selectively detectable, and thereby the possibility of detecting mutually overlapping signals of two or more light-emitting particles as a signal of one light-emitting particle is reduced substantially.

The intensity of light which is emitted from a light-emitting particle passing through a light detection region and reaches to a photodetector varies depending upon the position of the light-emitting particle in the light detection region. For example, in a case that a light-emitting particle is a particle which emits light with the irradiation of illumination light, the light intensity in the light detection region of the illumination light, typically, becomes the maximum approximately at the center of the light detection region (the light condensing region), and decreases from the maximum intensity point almost in the radial direction. Thus, the light intensity of a light-emitting particle becomes the maximum when the light-emitting particle crosses the approximate center of the light detection region, and as the position of the light-emitting particle approaches the circumference of the light detection region, the light intensity gradually reduces. Namely, the intensity distribution of the detected light which is emitted from a light-emitting particle in the light detection region is a bell shaped distribution as illustrated at FIG. 3C upper left, and for example, as drawn in FIG. 3A, the light intensity of the light-emitting particle γ which passes through the region drawn with the dotted line in the drawing becomes higher than the light intensities of the light-emitting particles α and β which pass through the outside of the region drawn with the dotted line (see FIG. 3B). Thus, briefly speaking, with reference to the signal intensity of a light-emitting particle, the area in which the light-emitting particle has passed within the light detection region will be specified. And, in the detection of a signal of a light-emitting particle from time series light intensity data, by setting a threshold value and detecting only the signal which has an intensity exceeding the threshold value as a significant signal, it becomes possible to "pick up" only a signal corresponding to a light-emitting particle having passed through the region which gives light intensity more than the threshold value. Moreover, as in FIG. 3C upper left, when a threshold value is increased in the order of Ith0→Ith1→Ith2, the region through which a picked-up light-emitting particle has passed will shrink in order of CV→qCV1→qCV2, as drawn in the sectional view and perspective view of FIG. 3C, lower left and lower right. In the other words, in the analysis processing of a signal on time series light intensity data, by setting a certain threshold value (for example, Ith1, Ith2), a region for detecting a single light-emitting particle, i.e., "apparent light detection region" (for example, qCV1, qCV2), is defined, and it becomes possible to selectively detect only a signal of a light-emitting particle which has passed through the inside of the apparent light detection region.

In addition, as noted above, in a case that the selection of a signal of a light-emitting particle is made with the height of the signal intensity, if two or more light-emitting particles enter into a light detection region simultaneously and there is almost no difference in the time of the peaks (maximum) of the signals of those light-emitting particles, irrespective of whether or not those light-emitting particles have passed the apparent light detection region, the signals of those light-emitting particles can be detected as a signal of one light-emitting particle without being distinguished mutually. However, because light-emitting particles are distributed in three dimensions in a sample solution, it is rare that two light-emitting particles enter into a light detection region simultaneously (unless the number density of a light-emitting particle becomes extremely high), and also, the intensity distribution of detected light from the light-emitting particle in the light detection region is a bell shaped distribution, wherein the intensity of a light-emitting particle decreases as the position of the light-emitting particle is closer to the circumference of the light detection region, and therefore, even if two light-emitting particles enter into the light detection region almost simultaneously and the maximum value of the intensity of those overlapped signals increases, it is considered to be lower as compared with the light intensity of a single light-emitting particle located near the center of the light detection region in most cases (since the number of light-emitting particles is smaller for particles having a higher light intensity, the probability that light-emitting particles of high light intensity overlap is extremely lower than the probability that light-emitting particles of low light intensity overlap). Accordingly, as noted, by setting a threshold value appropriately, the mutually overlapping signals of two or more light-emitting particles detected as a signal of one light-emitting particle is eliminated substantially.

In the structure of adjusting the size of an apparent light detection region by setting appropriately a threshold value in accordance with the above-mentioned present invention, a threshold value and the size of an apparent light detection region are associated by the following relational expressions. Namely, as illustrated in FIG. 3C upper left, in a case that an intensity distribution of detected light which is emitted from a light-emitting particle in a light detection region can be approximated with a Gauss function, using the maximum of the light intensity distribution, Imax (Imax is equivalent to the maximum light intensity of a single light-emitting particle); the half width at half maximum of the distribution, w; the background of the intensity, Ibg; and the cross-sectional radius (distance from the maximum intensity point) of the apparent light detection region, r; a threshold value Ith can be expressed by:

[Expression 1]

$$I_{th} = I_{max} \exp\left(-\frac{r^2}{2\pi w^2}\right) + I_{bg} \quad (1)$$

Supposing the cross sectional area S of the apparent light detection region (in the direction vertical to the moving direction) is approximately given by $S=\pi r^2$ (Although, strictly, the cross section of the light detection region is elliptical, it is approximated with a circle for the simplification of the calculation. The same in the following), the relation between the cross sectional area S of the apparent light detection region and the threshold value Ith is given by

[Expression 2]
$$S = 2w^2 \ln\left(\frac{I_{max}}{I_{th} - I_{bg}}\right) \quad (2)$$

In addition, when the intensity distribution of detected light which is emitted from a light-emitting particle in the light detection region can be approximated with a Lorentz function, the threshold value Ith can be expressed by:

[Expression 3]
$$I_{th} = wI_{max}\left(\frac{w}{r^2 + w^2}\right) + I_{bg}, \quad (3)$$

so that the relation between the cross sectional area S of the apparent light detection region and the threshold value Ith is given by:

[Expression 4]
$$S = \frac{\pi w^2 I_{max}}{I_{th} - I_{bg}} - \pi w^2 \quad (4)$$

By the way, in moving a light detection region at a scanning speed (moving speed) u in a sample solution, in a case that the number of light-emitting particle encompassed at a time in the apparent light detection region which has the volume V is always one, the number of light-emitting particles Pmax detected in a measuring time t is given by:

$$P\max = Sut/V \quad (5).$$

That is, when the number of light-emitting particles exceeds Pmax in the light measurement of the measuring time t, the number of light-emitting particles encompassed at a time in the apparent light detection region which has the volume V can be two or more. In the other words, in the present invention, the setting of the threshold value which renders the number of light-emitting particles encompassed at a time in the apparent light detection region to be substantially always be one or less is done so that the number of detected light-emitting particles Pth should fulfill the condition:

$$Pth \leq P\max \quad (6).$$

Accordingly, in a case that the intensity distribution of detected light which is emitted from a light-emitting particle in the light detection region can be approximated with a Gauss function, in accordance with Expression (5) and Expression (2), the condition that the number of light-emitting particles encompassed at a time in the apparent light detection region is substantially always one or less is realized by setting a threshold value so that

[Expression 5]
$$Pth \leq 2w^2 \ln\left(\frac{I_{max}}{I_{th} - I_{bg}}\right) \cdot \frac{ut}{V} \quad (7)$$

will be established. Also, in a case that the intensity distribution of detected light which is emitted from the light-emitting particle in the light detection region can be approximated with a Lorentz function, in accordance with Expression (5) and Expression (4), the condition that the number of light-emitting particles encompassed at a time in the apparent light detection region is substantially always one or less is realized by setting a threshold value so that

[Expression 6]
$$Pth \leq \left(\frac{\pi w^2 I_{max}}{I_{th} - I_{bg}} - \pi w^2\right) \cdot \frac{ut}{V} \quad (8)$$

will be established.

What should be minded with respect to the above-mentioned condition of Expression (7) or (8) is that, at a higher light-emitting particle concentration in a sample solution, the threshold value Ith which satisfies the condition of Expression (7) or (8) becomes higher, while, at a lower light-emitting particle concentration, the number of detected light-emitting particles Pth decreases. Thus, in order to obtain the number of light-emitting particles in good accuracy (enough for various analyses) under the condition that the number of light-emitting particles encompassed at a time in an apparent light detection region is substantially always one or less, it is preferable that an appropriate threshold value is selected according to the concentration of a light-emitting particle to be an observation object in a sample solution.

Operation processes of Scanning Molecule Counting Method

In the embodiment of the scanning molecule counting method in accordance with the present invention with the optical analysis device 1 as illustrated in FIG. 1A, concretely, there are conducted (1) a process of preparation of a sample solution containing light-emitting particles, (2) a process of measuring the light intensity of a sample solution and (3) a process of analyzing the measured light intensity. FIG. 4 shows the operation processes in this embodiment in the form of a flow chart.

(1) Preparation of a Sample Solution

The particle to be observed in the inventive method may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological particle (Typically, the sample solution is an aqueous solution, but not limited to this, and it may be an organic solvent or other arbitrary liquids). Also, the particle to be observed may be a particle which emits light by itself, or may be a particle to which a light emitting label (a fluorescence molecule, a phosphorescence molecule, and a chemiluminescent or bioluminescent molecule) is attached in an arbitrary manner.

(2) Measurement of the Light Intensity of a Sample Solution

In the process of the measurement of the light intensity in the optical analysis in accordance with the scanning molecule counting method of this embodiment, there is performed measuring the light intensity with driving the mirror deflector 17 to move the position of the light detection region within the sample solution (to scan in the sample solution) (FIG. 4—step 100). In the operation process, typically, after dispensing a sample solution into the well(s) 10 of the micro plate 9 and putting it on the stage of the microscope, when a user inputs to the computer 18 a command of a measurement start, the computer 18 executes programs (the process of changing the optical path in order to move the position of the light detection region in the sample solution, and the process of detecting light from the light detection region during the moving of the position of the light detection region) memorized in a storage device (not shown), and then illuminating the light detection region in the sample solution with the excitation light and measuring light intensity will be started. When the measurement was started, under the control of the operation process of the computer 18 according to the programs, from the light source 2, the light of the excitation wavelength of a light-emitting particle in the sample solution is emitted, and the mirror deflector 17 drives the mirror 7 (galvanomirror) to move the position of the light detection region in the well 10, and simultaneously with this, the photodetector 16 sequentially converts the detected light into an electric signal and transmits it to the computer 18, which generates the time series light intensity data from the transmitted signals and store it in an arbitrary manner. The photodetector 16 is typically a super high sensitive photodetector which can detect an arrival of a single photon, and thus the detection of light may be the photon counting performed in the manner of measuring sequentially the number of photons which arrive at the photodetector for every predetermined unit time (BIN TIME), for example, every 10 μs, during a predetermined time, and accordingly the time series light intensity data will be a time series photon count data.

The moving speed of the position of the light detection region during the measurement of the light intensity may be a predetermined velocity set arbitrarily, for example, experimentally or in order to meet the purpose of an analysis. In a case of acquiring the information on the number density or concentration based on the number of detected light emitting particles, the region size or volume through which the light detection region has passed is required, and therefore, preferably, the moving of the position of the light detection region is performed in a manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

By the way, regarding the moving speed of the position of the light detection region, in order to perform quantitatively precisely individual detection of a light-emitting particle to be observed from the measured time series light intensity data or the counting of the number of the light-emitting particles, it is preferable that the moving speed is set to a value quicker than the moving speed in the random motion, i.e., Brownian motion of a light-emitting particle. Since the light-emitting particle to be the observation object in this embodiment is a particle dispersed or dissolved in a solution and moving at random freely, its position moves with time owing to the Brownian motion. Thus, when the moving speed of the position of the light detection region is slower than the movement of a particle owing to the Brownian motion, the particle moves at random in the region as schematically drawn in FIG. 5A, whereby the light intensity changes at random (the excitation light intensity in the light detection region is reduced from the peak at the center of the region toward its outside), so that it becomes difficult to determine a significant light intensity change corresponding to each light-emitting particle (a signal indicating light from a light-emitting particle). Then, preferably, as drawn in FIG. 5B, the moving speed of the position of the light detection region is set to be quicker than the average moving speed of a particle by the Brownian motion (diffusional moving velocity) so that the particle will cross the light detection region in an approximately straight line and thereby the profile of the change of the light intensity corresponding to each particle becomes almost uniform in the time series light intensity data as illustrated in the upper row of FIG. 5C (When a light-emitting particle passes through the light detection region in an approximately straight line, the profile of the light intensity change is similar to the excitation light intensity distribution) and the correspondence between each light-emitting particle and light intensity can be easily determined.

Concretely, the time $\Delta t$ required for a light-emitting particle having a diffusion coefficient D to pass through the light detection region of radius Wo (confocal volume) by Brownian motion is given from Expression of the relation of mean-square displacement:

$$(2Wo)^2 = 6D \cdot \Delta t \tag{9}$$

as:

$$\Delta t = (2Wo)^2/6D \tag{10},$$

and thus, the velocity of the light-emitting particle moving by Brownian motion (diffusional moving velocity) Vdif, becomes approximately $$Vdif = 2Wo/\Delta t = 3D/Wo \tag{11}$$

Then, with reference to this, the moving speed of the position of the light detection region may be set to a value sufficiently quicker than Vdif. For example, when the diffusion coefficient of a light-emitting particle is expected to be about $D=2.0\times10^{-10}$ m$^2$/s, Vdif will be $1.0\times10^{-3}$ m/s, supposing Wo is about 0.62 μm, and therefore, the moving speed of the position of the light detection region may be set to its 10 times or more, 15 mm/s. In this regard, when the diffusion coefficient of a light-emitting particle is unknown, an appropriate moving speed of the position of the light detection region may be determined by repeating the executions of a preliminary experiment with setting various moving speeds of the position of the light detection region in order to find the condition that the profile of a light intensity variation becomes an expected profile (typically, similar to the excitation light intensity distribution).

(3) Analysis of Light Intensity

When the time series light intensity data of a light-emitting particle in a sample solution are obtained by the above-mentioned processes, detection of a signal corresponding to light from a light-emitting particle on the light intensity data; various analyses, such as the counting of light-emitting particles, calculation of a concentration of the light-emitting particle, may be performed in the computer 18 through processes in accordance with programs memorized in a storage device.

Figure 5B:
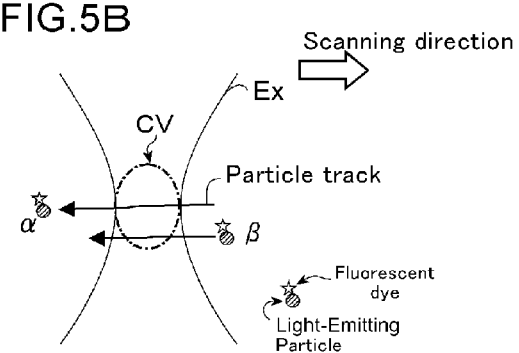
Figure 5C:
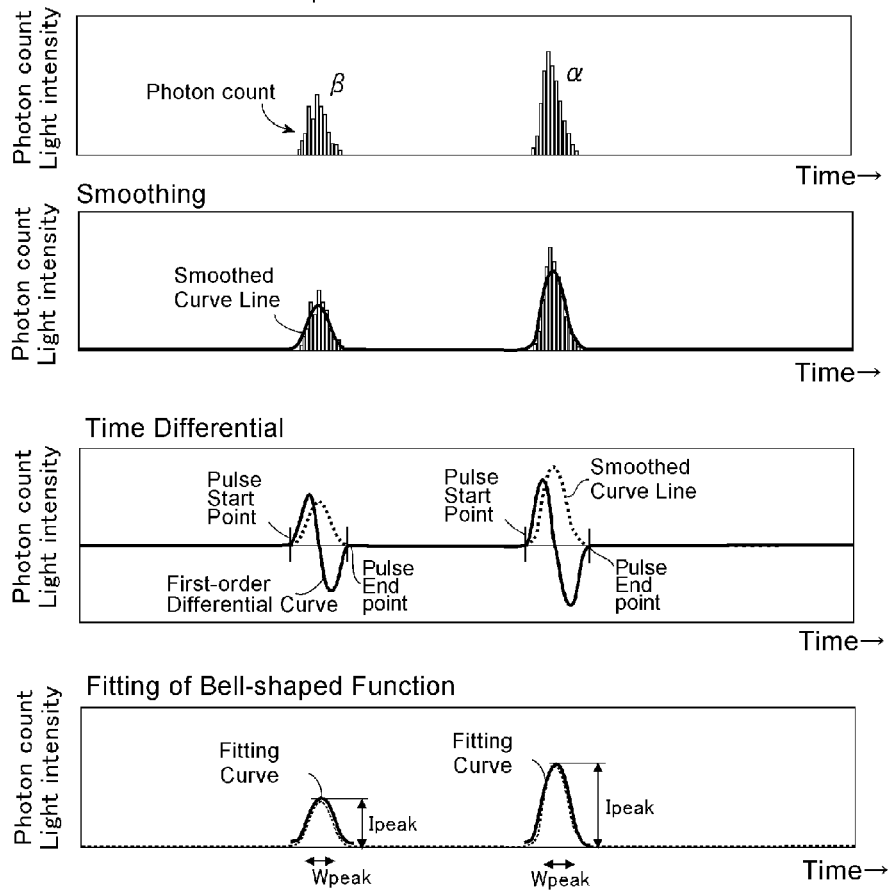

(i) Detection of a Signal Corresponding to a Light-Emitting Particle and Determination of its Number Density or Concentration When the track of one light-emitting particle in its passing through the light detection region is approximately straight as shown in FIG. 5B, the light intensity variation in the signal corresponding to the particle to be observed in the time series light intensity data has a bell shaped profile reflecting the light intensity distribution in the light detection region (determined by the optical system). Thus, basically in the scanning molecule counting method, when the time width Δτ for which the light intensity exceeding an appropriately set threshold value Io continues is in a predetermined range, the signal having the profile of the light intensity may be judged to correspond to one particle having passed through the light detection region, and thereby one light-emitting particle is detected. And a signal whose time width Δτ for which the light intensity exceeding the threshold value Io continues is not in a predetermined range is judged as noise or a signal of a contaminant. Further, when the light intensity distribution in the light detection region can be assumed as Gaussian distribution:

$$I = A \cdot \exp(-2t^2/a^2) \quad (12),$$

and when the intensity A and the width a, computed by fitting Expression (12) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

As an example of operational methods of conducting a collective detection and the counting of light-emitting particles from time series light intensity, a smoothing treatment is performed to the time series light signal data (FIG. 5C, the upper row "detected result (unsettled)") (FIG. 4—step 110, FIG. 5C mid-upper row "smoothing"). Although the light emitted by a light-emitting particle is stochastic so that gaps will be generated in data values in minute time, such gaps in the data value can be disregarded by the smoothing treatment. The smoothing treatment may be done, for example, by the moving average method. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differentiation value with time of the time series light intensity data after the smoothing treatment is computed (step 120). As illustrated in FIG. 5C, the mid-low row "time differential", in the time differential value of time series light signal data, the variation of the value increases at the time of the signal value change, and thereby, the start point and the end point of a significant signal can be determined advantageously by referring to the time differential value.

After that, a significant pulse signal is detected sequentially on the time series light intensity data, and it is judged whether or not the detected pulse signal is a signal corresponding to a light-emitting particle. Concretely, first, on the time series time-differential value data of the time series light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed time series light intensity data in the pulse existing region (FIG. 5C), the lower row "bell-shaped function fitting"), and then, parameters of the pulse of the bell-shaped function, such as the peak intensity (the maximum), Ipeak; the pulse width (full width at half maximum), Wpeak; the correlation coefficient in the fitting (of the least square method), etc. are computed (step 140). In this regard, although the bell-shaped function to be used in the fitting is typically Gauss function, it may be Lorentz type function. And it is judged whether or not the computed parameters of the bell-shaped function are within the respective ranges assumed for the parameters of the bell-shaped profile drawn by a pulse signal detected when one light-emitting particle passes a light detection region, i.e., whether or not each of the peak intensity, the pulse width and the correlation coefficient of the pulse is within the corresponding predetermined range (step 150). In this regard, while, at this step, with respect to the peak intensity of a pulse, it is judged whether or not the intensity is over the threshold value, as explained in detail later, in the inventive method, the threshold value is set in order to define an appropriate "apparent light detection region". Then, the signal, whose computed parameters of the bell-shaped function are judged to be within the ranges assumed in a light signal corresponding to one light-emitting particle, as shown in FIG. 6A left, is judged as a signal corresponding to one light-emitting particle, and thereby, one light-emitting particle will be detected. On the other hand, a pulse signal, whose computed parameters of the bell-shaped function are not within the assumed ranges, as shown in FIG. 6A right, is disregarded as noise.

The search and judgment of a pulse signal in the processes of the above-mentioned steps 130-150 are repetitively carried out in the whole region of the time series light signal data (Step 160). In this regard, although not illustrated, the number of the detected pulse signals may be counted during the search of pulse signals in the whole region of time series light intensity data. Also, the process of detecting individually signals of light-emitting particles from time series light intensity data may be conducted by an arbitrary way other than the above-mentioned way.

The number density or concentration of a light-emitting particle in time series light intensity data can be determined using the number (count value) of the signals corresponding to the respective light-emitting particles and the volume of the whole region which the light detection region has passed through during the acquisition of the time series light intensity data. However, the effective volume of the light detection region varies depending on the wavelength of excitation light or detected light, the numerical aperture of lenses and the adjustment condition of the optical system, and therefore, it is generally difficult to compute the effective volume of the light detection region from the design parameter values, and it is not easy to compute the whole volume which the light detection region has passed through, either. Thus, typically, the light intensity measurement, the detection of particles and the counting thereof are performed as explained above with a solution having a known light-emitting particle concentration (reference solution) under the same condition as that for the measurement of a sample solution to be tested, and then, from the number of detected light-emitting particles and the concentration of the light-emitting particle in the reference solution, the volume of the whole region which the light detection region has passed through, i.e., the relation between the detected number and the concentration of the light-emitting particle, may be determined. Preferably, the light-emitting particle of a reference solution may be a light emitting label (fluorescent dye etc.) having the same wavelength characteristic as the corresponding light-emitting particle. Concretely, for example, supposing the number of detected the light-emitting particles is N in a reference solution of the particle concentration (number density) C, the volume Vt of the whole region which the light detection region has passed through is given by:

$$Vt = N/C \quad (13)$$

Alternatively, the plurality of solutions of different concentrations are prepared as reference solutions and the measurement is performed for each of the solutions, and then, the average value of the computed Vt is determined as the volume Vt of the whole region which the light detection region has passed through. Thus, when Vt is given, the concentration (number density) c of the light-emitting particle of the sample solution, whose counting result of the particles is n, is given by:

$$c = n/Vt \quad (14)$$

In this regard, the volume of the light detection region and the volume of the whole region which the light detection region has passed through may be given by an arbitrary method, for instance, using FCS and FIDA, instead of the above-mentioned method. Further, in the optical analysis device of this embodiment, there may be previously memorized in a storage apparatus of the computer 18 the information on the relations (Expression (13)) between concentrations C and particle numbers N of various standard particles for assumed moving patterns of the light detection region, so that a user of the device can appropriately use the memorized information on the relation in conducting an optical analysis.

(ii) The Setting of a Threshold Value

In the above-mentioned step 150, in judging whether or not a significant pulse signal on time series light intensity data is a signal of a light-emitting particle, it is judged whether or not the peak intensity obtained by carrying out the fitting of a bell shaped function to the pulse signal on time series light intensity data is over a threshold value. In this threshold judgment, in the inventive method, the threshold value is set not only for discriminating between a signal of a light-emitting particle and noise, but also for defining an "apparent light detection region", and a signal of a light-emitting particle which has passed through the "apparent light detection region" is detected as a signal of a light-emitting particle. The setting of this threshold value is done preferably in order that the number of light-emitting particle encompassed in an apparent light detection region is substantially always one or less, namely, in order that the above-mentioned condition of Expression (7) or (8) is satisfied.

However, it is difficult to determine immediately the threshold value which satisfies the above-mentioned condition of Expression (7) or (8). Thus, typically, in the light intensity data obtained by measuring the light intensities of several reference solutions having different light-emitting particle concentrations as explained above, the detection and counting of particles are performed with various threshold values, and the threshold value which gives the result in which the number of pulses detected as a signal of a light-emitting particle is proportional to the light-emitting particle concentration is searched (It can be considered that each pulse signal corresponds to a single light-emitting particle when the number of pulses is proportional to the light-emitting particle concentration in a low concentration range to a high concentration range of a light-emitting particle), and thereby, the appropriate threshold value may be determined beforehand for various light-emitting particle concentrations. In the setting of a threshold value in a case of conducting a test by the scanning molecule counting method for a certain sample solution, an appropriate threshold value is chosen among the threshold values determined in accordance with an expected light-emitting particle concentration. As described in Embodiment 1 described later, in a typical experimental condition, in the setting of the threshold value for distinguishing between a signal of a light-emitting particle and noise, the above-mentioned condition of Expression (7) or (8) becomes unsatisfied at a light-emitting particle concentration exceeding beyond 100 pM. Accordingly, a threshold value for distinguishing between a signal of a light-emitting particle and noise may be employed in light-emitting particle concentrations of 0-100 pM, while, in light-emitting particle concentrations of 100 pM-1 nM, a higher threshold value may be selected.

(iii) Conversion of the Number of Pulses

As noted, in a case that the number of light-emitting particles (the number of pulses) is counted with selecting a threshold value which is changed depending upon a light-emitting particle concentration, it becomes difficult to compare the results of the numbers of light-emitting particles obtained using mutually different threshold values. As already noted, the threshold value satisfying the above-mentioned condition of Expression (7) or (8) will become high at a high light-emitting particle concentration, while the number of detected light-emitting particles reduces at a low light-emitting particle concentration, and therefore, in order to measure the number of light-emitting particles in good accuracy, it is preferable to select an appropriate threshold value according to the light-emitting particle concentration in a sample solution; however, since the number of light-emitting particles detected for a sample solution of a certain light-emitting particle concentration changes with threshold values, the numbers of light-emitting particles detected with different threshold values cannot be compared mutually as they are. For instance, as noted, in a typical measurement condition, threshold values appropriate for a sample solution of a light-emitting particle concentration less than 100 pM and a sample solution of a light-emitting particle concentration around 1 nM are mutually different, and it is preferable to count the number of light-emitting particles with the corresponding threshold value in each case. However, in comparing the number of light-emitting particles of the sample solution of a light-emitting particle concentration less than 100 pM with the number of light-emitting particles of the sample solution of a light-emitting particle concentration around 1 nM, the difference of the numbers of light-emitting particles cannot be detected as it is. Then, in one manner of the inventive method, it is tried to compute, from the number of light-emitting particles obtained using a certain threshold value, the number of light-emitting particles to be detected when another threshold value is set.

More in detail, it is considered that the ratio of the number of pulses Pth2 obtained with a certain threshold value, Ith2, and the number of pulses Pth1 to be obtained with a different threshold value Ith1 is equal to the ratio of the cross sectional area Sth2 of the apparent light detection region in the direction vertical to the scanning direction when the threshold value Ith2 is set and the cross sectional area Sth1 of the apparent light detection region in the direction vertical to the scanning direction when the threshold value Ith1 is set, and accordingly, the number of pulses Pth1 to be obtained with the different threshold value Ith1 is given by:

$$Pth1 = (Sth1/Sth2) \cdot Pth2 \quad (15)$$

Sth1 and Sth2 are given by Expression (2) [in a case of Gauss function] and Expression (4) [in a case of Lorentz function], respectively, and thus, when the maximum Imax of the light intensity distribution in the light detection region, the half width at half maximum w of the distribution, the threshold value Ith and the background Ibg are known, the conversion from the number of pulses Pth2 obtained with the threshold value Ith2 to the number of pulses Pth1 to be obtained with the different threshold value Ith1 will be done using Expression (15).

The maximum Imax of the light intensity distribution in the light detection region, the half width at half maximum w of the distribution and the background Ibg may be determined by an arbitrary way. In one method, for instance, the maximum Imax of the light intensity distribution, the half width at half maximum w of the distribution and the background Ibg can be determined from the relation between a threshold value in a case that the number of light-emitting particles encompassed in the light detection region is always one or less and the number of light-emitting particles obtained with the threshold value. Concretely, first, using the cross sectional area S of the apparent light detection region in the direction vertical to the scanning direction, the scanning speed u and the light-emitting particle concentration c, the number of light-emitting particles P (Ith) detected with a threshold value Ith in the light intensity data of the measuring time t is given by:

$$P(Ith) = cN_A Sut \tag{16}$$

Here, $N_A$ is Avogadro's number. Supposing the cross sectional area S of the apparent light detection region in the direction vertical to the scanning direction is given as $S = \pi r^2$ [r is the cross-sectional radius of the apparent light detection region],

[Expression 7]

$$r = \sqrt{\frac{P(Ith)}{cN_A ut\pi}} \tag{17}$$

is obtained from Expression (16). Thus, with respect to a solution having a known concentration of a certain light-emitting particle, when a plurality of sets of a threshold value Ith and the cross-sectional radius r of the apparent light detection region obtained based on the number P(Ith) of light-emitting particles at the threshold value are obtained, it becomes possible to compute the maximum Imax of the light intensity distribution and the half width at half maximum w of the distribution by using Expression (1) or (3). More concretely, for example, as shown later in Embodiment 2, in light intensity data obtained with respect to a solution having a known concentration of a light-emitting particle, while the threshold value Ith is changed, the number of light-emitting particle P(Ith) is counted with each threshold value, so that the cross-sectional radius r of the apparent light detection region can be computed from the number of light-emitting particle P(Ith). After this, by fitting Expression (1) or (3) to threshold values Ith for the series of cross-sectional radii r of the apparent light detection regions, the maximum Imax of the light intensity distribution and the half width at half maximum w of the distribution can be determined. (the background may be appropriately set with reference to light intensity data, not based on the fitting.)

Thus, as described above, when the conversion of the number of light-emitting particles obtained using a certain threshold value into the number of light-emitting particles to be obtained using another threshold value becomes possible, it becomes easy to compare the results of the numbers of light-emitting particles obtained using mutually different threshold values.

(iv) Estimation of a Light-Emitting Particle Concentration Using a Threshold Value which Give a Fixed Number of Light-Emitting Particles From the above-mentioned Expression (16), the light-emitting particle concentration c is given by:

$$c = P(Ith)/(N_A Sut) \tag{18},$$

and the cross sectional area S of an apparent light detection region is a function of the threshold value Ith given by Expression (2) or (4). Thus, the light-emitting particle concentration c can be computed using P (Ith), Ith, and parameters of the light intensity distribution in the light detection region, Imax, w, and Ibg. In this respect, the relation among a certain threshold value Ith, the number of light-emitting particles P(Ith) obtained using the threshold value and the concentration c is given by:
(in a case that a light intensity distribution can be approximated with a Gauss function)

[Expression 8]

$$I_{th} = I_{max} \exp\left(-\frac{P(I_{th})}{2\pi w^2 ut N_A c}\right) + I_{bg} \tag{19}$$

(in a case that a light intensity distribution can be approximated with a Lorentz function)

[Expression 9]

$$I_{th} = \frac{w I_{max} ut N_A c}{P(I_{th}) + \pi w^2 ut N_A c} + I_{bg}, \tag{20}$$

and therefore, the parameters of a light intensity distribution, Imax, w, and Ibg can be obtained by searching for threshold values Itho giving a certain fixed number of light-emitting particles Po in the light intensity data obtained with respect to various solutions having known light-emitting particle concentrations and subsequently fitting Expression (19) or (20) to a plurality of the sets of light-emitting particle concentration c and threshold value Itho. Then, in determining the concentration of the light-emitting particle in an arbitrary sample solution from the light intensity data measured with the sample solution, the threshold value Itho which gives the above-mentioned fixed number of light-emitting particle Po in the light intensity data is detected, and thereby, the concentration of light-emitting particle is determined from the detected Itho and Po. According to this way, by setting the fixed number of light-emitting particle Po to the value with which the above-mentioned condition of Expression (7) or (8) is satisfied in the whole range of the light-emitting particle concentrations of sample solutions to be observation objects, the determination of light-emitting particle concentration becomes possible irrespective of the light-emitting particle concentrations in the sample solutions with avoiding errors of the number of light-emitting particles resulting from two or more light-emitting particles being encompassed at a time in an apparent light detection region.

Thus, according to the above-mentioned inventive method, by appropriately setting a threshold value in detecting a signal of a light-emitting particle from light intensity data in the scanning molecule counting method, the individual detection of single light-emitting particles becomes possible under conditions that no overlapped signals of two or more light-emitting particles exist substantially, so that the information on the number, concentration or number density of light-emitting particles can be acquired more accurately. And, according to the present invention, especially, the concentration range of a light-emitting particle for which the scanning molecule counting method can be used is expanded to the higher concentration side.

In order to verify the validity of the present invention explained above, the experiments described below were conducted. In this regard, it should be understood that the following embodiments illustrate the validity of the present invention only, not intended to limit the scope of the present invention.

Embodiment 1

Change of the Threshold Value for Detection of a Light-Emitting Particle Signal

It was verified that, in the detection of a signal of a light-emitting particle from time series light intensity data obtained in a light measurement by a scanning molecule counting method, an "apparent light detection region" was adjusted by changing a threshold value for judging a signal of a light-emitting particle.

For sample solutions, there were prepared solutions containing a fluorescent dye ATTO633 (Sigma-Aldrich, Cat. No. 18620) as a light-emitting particle at 1 pM, 10 pM, 100 pM and 1 nM, respectively, in a phosphate buffer (containing 0.05% Tween 20). In the light measurement, a single molecule fluorescence measuring apparatus MF-20 (Olympus Corporation), equipped with the optical system of a confocal fluorescence microscope and a photon counting system, was used as the optical analysis device, and time series light intensity data (photon count data) were acquired for the above-mentioned respective sample solutions in accordance with the manner explained in the above-mentioned "(2) Measurement of the light intensity of a sample solution". In that time, a 633-nm laser light was used for excitation light, and, using a band pass filter, the light of the wavelength bands, 660 to 710 nm, was measured, and time series light intensity data was generated. The moving speed of the position of the light detection region in the sample solution was set to 30 mm/second; BIN TIME was set to 10 μsec.; and for the respective sample solutions, the measurement for 2 seconds was performed three times. After the light intensity measurement, in accordance with the procedures described in the above-mentioned "(3) (i) Detection of a signal corresponding to a light-emitting particle", the smoothing treatment was applied to the time series light intensity data acquired with each sample solution, and after determining the start points and the end points of pulse signals in the smoothed data, the fitting of a Gauss function to each pulse signal was carried out by the least square method, and a peak intensity, a pulse width (full width at half maximum) and a correlation coefficient (in the Gauss function) were determined.

Then, only the pulse signal satisfying the following conditions:

20 μsec.<pulse width<400 μsec.

Peak intensity>Threshold value $I_{th}[pc/10$ μsec.$]$

Correlation coefficient>0.95     (A)

was judged as a signal corresponding to a light-emitting particle, while a pulse signal which did not satisfy the above-mentioned conditions was disregarded as noise. In this regard, the threshold value Ith was set in the range of 0.5-3.0 (photon/10 μsec.) as explained below. (In this connection, the reason of the appearance of the indication below a decimal point in photon count is because of the smoothing of photon count data. Namely, the photon count value is treated as a continuous value by the smoothing treatment.)

FIGS. 7A and 7B each are graphs in which the numbers of pulses in cases of setting threshold value, Ith=0.5 [pc/10 μsec], and threshold value, Ith=2.0 [pc/10 μsec.] in the above-mentioned condition (A) (the number of signals detected as a signal of a light-emitting particle) are plotted against light-emitting particle concentration, and FIG. 7C shows the change of the number of pulses against concentration in changing the threshold value Ith to 3.0 by 0.5 (Each point is the average of three measurements). With reference to these drawings, in any cases, the number of pulses monotonically increased with the light-emitting particle concentration (This shows that the light-emitting particle concentration in an arbitrary solution can be determined by the scanning molecule counting method by measuring the number of pulses using a solution of a known light-emitting particle concentration beforehand). However, as seen from FIG. 7A or FIG. 7C, in the case of a small threshold value (~1.5), the concentration was lower than the straight line extrapolated with the numbers of pulses from 1 pM to 100 pM and the linearity of the number of pulses to the concentration was not maintained in the concentrations beyond 100 pM. This is considered to be because overlapped signals of two or more light-emitting particles were detected as the signal of one light-emitting particle due to the high light-emitting particle concentration. On the other hand, as clearly seen from FIG. 7C or FIG. 7B, when the threshold value was increased (2.0~), the number of pulses was approximately proportional to the light-emitting particle concentration in the whole observed concentration range.

Taking into account that only a signal with high light intensity is selected owing to the increase of the threshold value and that the intensity distribution of detected light which is emitted from a light-emitting particle in the light detection region is approximately bell shaped (This is understood also from the fact that the shape of each pulse signal is approximately bell shaped), according to the above-mentioned results, it is considered that the existence region of the detected light-emitting particles (namely, the apparent light detection region) is reduced to a region where an intensity is high in the light intensity distribution owing to the increase of the threshold value, and thereby, the possibility that the overlapped signals of two or more light-emitting particles will be detected decreases substantially so that substantially only a signal of a single light-emitting particle will be detected as a signal of a light-emitting particle. Thus, according to the above-mentioned results, it has been confirmed that an "apparent light detection region" is adjusted by setting a threshold value appropriately according to a light-emitting particle concentration, and thereby a single light-emitting particle can be detected individually, making it possible to acquire more accurately information, including the number, concentration, or number density of light-emitting particles, by defining the "apparent light detection region" so that the number of the light-emitting particles encompassed will be substantially always one or less.

Embodiment 2

Determination of an Intensity Distribution of Light of a Light-Emitting Particle in a Light Detection Region The parameters (the peak intensity Imax, the half width at half maximum w, background Ibg) of an intensity distribution of detected light which is emitted from a light-emitting particle in a light detection region have been determined from a cross-sectional radius r of an apparent light detection region (in the direction vertical to its moving direction) and a threshold value Ith. The cross-sectional radius r of an apparent light detection region (in the direction vertical to its moving direction) was computed, using Expression (17), from the numbers of light-emitting particles P (Ith) obtained with changing the threshold value Ith on the light intensity data obtained for a sample solution having a known light-emitting particle concentration where the number of light-emitting particles in the light detection region was substantially always one or less. Concretely, in the light intensity data obtained with the sample solution of 10 pM ATTO633 of Embodiment 1, the numbers of light-emitting particles P(Ith) were detected with changing the threshold value Ith, and the cross-sectional radius r of the apparent light detection region was computed with Expression (17) for each of the numbers of light-emitting particles P(Ith). FIG. 8A is a drawing in which the threshold values Ith are plotted against the cross-sectional radius r of the apparent light detection region (In this connection, the data points actually obtained in this drawing are □ points of the right half, and the data points of the left half are points given by reversing the data of the right half on the zero point axis as the axis of symmetry). It should be understood that the plot points in FIG. 8A show the profile of an intensity distribution of detected light which is emitted from a light-emitting particle in a light detection region (in the cross section in the direction vertical to the moving direction of the light detection region). Namely, as understood from Expression (1) or (3), the cross-sectional radius r of an apparent light detection region defines the line area where a light-emitting particle having an intensity equal to the threshold value Ith exists, and therefore, the relation between a threshold value Ith and the cross-sectional radius r of an apparent light detection region corresponds to the relation between the distance of the existence position of a light-emitting particle from the center (maximum intensity point) of the light detection region and the intensity of detected light which is emitted from the light-emitting particle at its position.

It was shown that the shape of the distribution of plots in FIG. 8A was well fit to the shape of a Lorentz function. Then, in the fitting of Expression (3) using the nonlinear least square method to the data of FIG. 8A (solid curve in the drawing), the peak intensity Imax of the intensity distribution of detected light which was emitted from a light-emitting particle in a light detection region was computed to be 5.81 [pc/10 μsec.], w was computed to be 0.57 [μm] and Ibg was computed to be 0.0 [pc/10 μsec.].

Thus, it has been confirmed that, according to the above-mentioned method, using a threshold value Ith and the number of light-emitting particles P(Ith), parameters of an intensity distribution of detected light which is emitted from a light-emitting particle in a light detection region can be computed so that the intensity distribution of light from a light-emitting particle in the light detection region can be determined approximately.

Embodiment 3

Conversion of the Number of Pulses

By the way described in "(3) (iii) Conversion of the Number of Pulses", the numbers of light-emitting particles detected from the light intensity data obtained in Embodiment 1 with different threshold values were converted into the numbers of light-emitting particles to be detected when another threshold value was used. Concretely, the number of light-emitting particles detected with threshold value=2.0 [pc/10 μsec.] of the sample solution of 100 pM ATTO633 and the number of light-emitting particles detected with threshold value=3.0 [pc/10 μsec.] of the sample solution of 1 nM ATTO633 each were converted with Expression (15) and Expression (4) into the number of light-emitting particles to be detected when the signal detection of a light-emitting particle was performed with threshold value=1.0 [pc/10 μsec.]. In this connection, in that time, for the respective parameters in Expression (4), the values obtained in Embodiment 2, i.e., Imax=5.81, w=0.57, and Ibg=0.0, were used.

FIG. 8B is graphs in which there are plotted against light-emitting particle concentration the numbers of light-emitting particles detected in performing the signal detection of a light-emitting particle with threshold value=1.0 [pc/10 μsec.] (before conversion), and the values obtained by converting the number of light-emitting particles of the sample solution of 100 pM ATTO633 detected with threshold value=2.0 [pc/10 μsec.] and the number of light-emitting particles of the sample solution of 1 nM ATTO633 detected with threshold value=3.0 [pc/10 μsec.] into the numbers of light-emitting particles to be detected when the signal detection of a light-emitting particle is performed with threshold value=1.0 [pc/10 μsec.], respectively (after conversion). With respect to the number of light-emitting particles of the sample solution of 100 pM ATTO633 detected with threshold value=2.0 [pc/10 μsec.], while the number was 2093.7 (the average of three measurements) in the case of threshold value=1.0 [pc/10 μsec.], the number [917 (the average of three measurements)] in the case of using threshold value=2.0 [pc/10 μsec.] was converted into 2316.3 in the case of threshold value=1.0 [pc/10 μsec.]. Also, with respect to the number of light-emitting particles of the sample solution of 1 nM ATTO633 detected with threshold value=3.0 [pc/10 μsec.], while the number was 8264.3 (the average of three measurements) in the case of threshold value=1.0 [pc/10 μsec.], the number [6293.3 (the average of three measurements)] in the case of using threshold value=3.0 [pc/10 μsec.] was converted into 32365.7 in the case of threshold value=1.0 [pc/10 μsec.]. In addition, as understood from FIG. 8B, when the signals of light-emitting particles were detected with threshold value=1.0 [pc/10 μsec.], similarly to the case shown in Embodiment 1, the number of pulses in the light-emitting particle concentrations of 100 pM~1 nM was much less than the values linearly extrapolated from the values in the lower concentration range; on the other hand, the numbers of pulses in the light-emitting particle concentration of 100 pM~1 nM obtained by the above-mentioned conversion became closer to the value linearly extrapolated from the values of the lower concentration range therefrom.

This result has suggested that, from the number of light-emitting particles detected with a certain threshold value, the number of light-emitting particles to be detected with another threshold value can be estimated by using Expression (15) and Expression (2) or (4). According to this way, for at least two sample solutions for which the threshold values satisfying Expression (7) or (8) are mutually different, even when the numbers of light-emitting particles are detected using the respective different threshold values, by converting those numbers of light-emitting particles into the numbers of light-emitting particles to be detected with the same threshold value, it becomes possible to compare those mutually. For instance, there becomes possible an analysis in which, after performing the detection of the number of light-emitting particles for a sample solution of high light-emitting particle concentration with a high threshold value satisfying Expression (7) or (8), the number of detected light-emitting particles is converted into the number of light-emitting particles to be detected with a threshold value which does not satisfy Expression (7) or (8) intrinsically, and then, the number of light-emitting particle obtained by the conversion is compared with the number of light-emitting particles of a sample solution of a low light-emitting particle concentration.

Embodiment 4

Estimation of a Light-Emitting Particle Concentration with a Threshold Value which Gives a Fixed Number of Light-Emitting Particles Using the time series light intensity data of each sample solution obtained in Embodiment 1, it has been confirmed that a light-emitting particle concentration could be estimated based on a threshold value which gives a certain fixed number of light-emitting particles. Concretely, first, in the time series light intensity data of each sample solution, the threshold value with which the number of light-emitting particles became 20 was determined. FIG. 9 shows the threshold values (black dot) with which the number of light-emitting particles became 20 against light-emitting particle concentration, and the curve obtained by carrying out the fitting of Expression (20) [Lorentz function] to the points of those threshold values using a nonlinear least square method (solid line). As understood from the drawing, the threshold values with which the number of light-emitting particles became 20 monotonically increased with the increase of the light-emitting particle concentration, and were well coincident with the fitting curve of Expression (20). The parameters in Expression (20) were Imax=8.7 [pc/10 μsec.] and w=2.9 μm, respectively. Thus, it was confirmed that, in the light intensity data of a sample solution having known concentration, the light-emitting particle concentration in the sample solution is detectable by detecting a threshold value which gives a fixed number of light-emitting particles.

As understood from the results of the above-mentioned embodiments, in accordance with the above-mentioned inventive method, an "apparent light detection region" is defined by setting appropriately a threshold value for detection of a signal of a light-emitting particle in the scanning molecule counting method so that it becomes possible to detect selectively substantially only a signal of a light-emitting particle which passed through the inside of the apparent light detection region. And, since the "apparent light detection region" is narrower than an actual light detection region, the possibility that overlapped signals of two or more light-emitting particles are detected as a signal of a light-emitting particle is reduced substantially. Therefore, a signal of a single light-emitting particle is individually detected with sufficient accuracy, and the number of light-emitting particles corresponding to the light-emitting particle concentration in a sample solution becomes detectable. According to this structure, the scanning molecule counting method becomes well usable even when a light-emitting particle concentration in a sample solution is comparatively high and the possibility that a condition that two or more light-emitting particles are encompassed at a time in the actual light detection region occurs is high, and therefore the range of the light-emitting particle concentration to which the scanning molecule counting method is applicable is expanded.

The invention claimed is:

1. An optical analysis method which detects light from a light-emitting particle dispersed and moving at random in a sample solution using an optical system of a confocal microscope or a multiphoton microscope, comprising steps of:
moving a position of a light detection region of the optical system in the sample solution by changing an optical path of the optical system;
measuring light intensity from the light detection region with moving the position of the light detection region in the sample solution to generate light intensity data; and
individually detecting a signal indicating light of a light-emitting particle on the light intensity data;
wherein in the step of individually detecting a signal indicating light of a light-emitting particle, a signal which has an intensity exceeding a threshold value is detected selectively as a signal indicating light of the light-emitting particle and the threshold value is set so that a signal indicating light from a light-emitting particle encompassed in a region narrower than the light detection region in the light detection region is detected selectively.

2. The method of claim 1, wherein an intensity distribution of detected light which is emitted from a light-emitting particle in the light detection region is a distribution in which an intensity of detected light which is emitted from the light-emitting particle reduces from a maximum intensity point in the light detection region toward a circumference of the light detection region.

3. The method of claim 1, wherein the threshold value is set so that the number of the light-emitting particle encompassed at a time in the region narrower than the light detection region is substantially one or less.

4. The method of claim 3, further comprising a step of counting a number of the selectively detected signals to determine the number of the light-emitting particles encompassed in the region narrower than the light detection region.

5. The method of claim 4, further comprising a step of determining a number density or a concentration of the light-emitting particle based on the determined number of the light-emitting particles.

6. The method of claim 4, wherein a number of the light-emitting particles to be detected when a threshold value different from the threshold value is set is computed from the determined number of the light-emitting particles based on the intensity distribution of detected light which is emitted from the light-emitting particle in the light detection region.

7. The method of claim 6, further comprising a step of determining a number density or a concentration of the light-emitting particle based on the computed number of the light-emitting particles.

8. The method of claim 3, wherein a threshold value with which the number of the selectively detected signals indicating light from the light-emitting particle becomes a predetermined number is determined and a number density or a concentration of the light-emitting particle is determined based on a height of the threshold value.

9. The method of claim 1, wherein the light-emitting particle is a particle which emits light when irradiated with excitation light, and the intensity distribution of detected light which is emitted from the light-emitting particle in the light detection region conforms with an intensity distribution of the excitation light in the light detection region.

10. The method of claim 1, wherein the position of the light detection region is moved at a velocity quicker than a diffusion moving velocity of the light-emitting particle in the sample solution.

* * * * *